(12) United States Patent
Yu et al.

(10) Patent No.: US 11,612,438 B2
(45) Date of Patent: Mar. 28, 2023

(54) NAVIGATION SYSTEM AND METHOD FOR MEDICAL OPERATION BY A ROBOTIC SYSTEM USING A TOOL

(71) Applicant: POINT ROBOTICS MEDTECH INC., Hsinchu (TW)

(72) Inventors: Shou-An Yu, Hsinchu (TW); Bang-Hao Dai, Hsinchu (TW); Che-Wei Su, Hsinchu (TW); Hao-Kai Chou, Hsinchu (TW); Chia-Ho Yen, Hsinchu (TW); Chih-Min Yang, Hsinchu (TW); Shyue-Cherng Juang, Hsinchu (TW)

(73) Assignee: POINT ROBOTICS MEDTECH INC., Hsinchu (TW)

( * ) Notice: Subject to any disclaimer, the term of this patent is extended or adjusted under 35 U.S.C. 154(b) by 422 days.

(21) Appl. No.: 16/122,861

(22) Filed: Sep. 5, 2018

(65) Prior Publication Data
US 2020/0069373 A1      Mar. 5, 2020

(51) Int. Cl.
*A61B 34/20* (2016.01)
*A61B 5/06* (2006.01)
(Continued)

(52) U.S. Cl.
CPC ............ *A61B 34/20* (2016.02); *A61B 1/0005* (2013.01); *A61B 1/00045* (2013.01);
(Continued)

(58) Field of Classification Search
CPC ....... A61B 34/20; A61B 5/066; A61B 1/0005; A61B 1/00039; A61B 5/062; A61B 2090/373; A61B 2034/2057; A61B 2034/2065; A61B 2034/2072; A61B 2034/302; A61B 2034/304; A61B 2505/05; A61B 5/064; A61B 34/37; A61B 34/74; A61B 17/1671; A61B 2090/5025;
(Continued)

(56) References Cited

U.S. PATENT DOCUMENTS

| 7,831,292 | B2 | 11/2010 | Quaid et al. | |
| 8,491,604 | B2* | 7/2013 | Stuart | A61B 34/70 |
| | | | | 606/130 |
| 9,603,665 | B2 | 3/2017 | Bowling et al. | |
| 10,058,396 | B1 | 8/2018 | Genova et al. | |
| 2008/0161829 | A1* | 7/2008 | Kang | B25J 9/101 |
| | | | | 606/130 |

(Continued)

FOREIGN PATENT DOCUMENTS

| CN | 101160104 A | 4/2008 |
| CN | 105636541 A | 6/2016 |

(Continued)

*Primary Examiner* — Joseph M Santos Rodriguez
*Assistant Examiner* — Maria Christina Talty
(74) *Attorney, Agent, or Firm* — ScienBiziP, P.C.

(57) ABSTRACT

A navigation method for a medical operation and implemented by a robotic system is provided. The method includes the steps of: receiving, at a processor of the robotic system, at least one set of navigation data; receiving or generating at least one three-dimensional model of the virtual object in the navigation data; calculating the navigation data to generate a virtual environment and at least one navigation instruction; and presenting, at a user interface associated with the robotic system, the virtual environment and/or the navigation instruction to a user of the robotic system for the user to refer to during the medical operation.

34 Claims, 17 Drawing Sheets

(51) Int. Cl.
  *A61B 1/00* (2006.01)
  *G06T 19/00* (2011.01)
  *A61B 90/00* (2016.01)
  *A61B 34/30* (2016.01)

(52) U.S. Cl.
  CPC .............. *A61B 5/062* (2013.01); *A61B 5/066* (2013.01); *G06T 19/003* (2013.01); *G06T 19/006* (2013.01); *A61B 2034/2057* (2016.02); *A61B 2034/2065* (2016.02); *A61B 2034/2072* (2016.02); *A61B 2034/302* (2016.02); *A61B 2034/304* (2016.02); *A61B 2090/373* (2016.02); *G06T 2219/004* (2013.01); *G06T 2219/028* (2013.01)

(58) Field of Classification Search
  CPC ............ A61B 90/50; A61B 2090/0807; A61B 2017/00115; A61B 34/10; A61B 90/361; A61B 2017/00119; A61B 2034/105; A61B 2034/102; A61B 2034/107; A61B 90/37; A61B 2034/2061; A61B 34/25; A61B 2090/3983; A61B 2034/2055; G06T 19/003; G06T 19/006; G06T 2219/004; G06T 2219/028; G06T 2210/41; G06T 19/00
  See application file for complete search history.

(56) References Cited

U.S. PATENT DOCUMENTS

| | | | |
|---|---|---|---|
| 2009/0088634 A1* | 4/2009 | Zhao | B25J 9/1656 600/425 |
| 2012/0184951 A1* | 7/2012 | Viola | A61B 18/1445 606/34 |
| 2013/0131867 A1* | 5/2013 | Olds | A61B 34/30 700/260 |
| 2013/0172905 A1 | 7/2013 | Iorgulescu et al. | |
| 2016/0030115 A1 | 2/2016 | Shen et al. | |
| 2016/0183841 A1* | 6/2016 | Duindam | A61M 25/01 600/424 |
| 2016/0206375 A1 | 7/2016 | Abbasi et al. | |
| 2016/0338782 A1* | 11/2016 | Bowling | A61B 17/1675 |
| 2017/0084027 A1 | 3/2017 | Mintz et al. | |
| 2017/0265947 A1 | 9/2017 | Dyer et al. | |
| 2017/0319302 A1* | 11/2017 | Mozes | A61B 34/76 |

FOREIGN PATENT DOCUMENTS

| | | | | |
|---|---|---|---|---|
| CN | 107970060 A | | 5/2018 | |
| CN | 108175503 A | | 6/2018 | |
| CN | 108472095 A | | 8/2018 | |
| KR | 20080047318 A | * | 5/2008 | ............ A61B 34/77 |
| TW | 201717837 A | | 6/2017 | |
| WO | WO-2007136771 A2 | * | 11/2007 | ............ A61B 34/10 |
| WO | WO-2017020081 A | * | 2/2017 | ............ A61B 34/37 |
| WO | 2017147596 A1 | | 8/2017 | |

* cited by examiner

NAVIGATION SYSTEM AND METHOD FOR MEDICAL OPERATION BY A ROBOTIC SYSTEM USING A TOOL

FIELD

The present disclosure relates to robotic system, and more particularly to a method for providing navigation instructions to the user in computer-assisted surgeries performed by the robotic system.

BACKGROUND

Numerous medical operations (e.g., a surgery) require high manual precision on the part of the surgeon. For example, surgical orthopedic operations require the surgeon to mill, drill or saw a bone of a subject at a precise location and at a precise angle in order to fit a given implant into the bone or to shape the bone to create a desired geometric profile. Such operations are usually performed by free-hand, with the surgeon holding a specific surgical instrument and following a trajectory based on anatomical landmarks. Accuracy of the surgical operations is thus dependent on the skill of the surgeon in following the predetermined plan with the hand-held surgical instrument.

Taking the advantages of information technology and robotics, computer assisted surgery has offered a reliable option in improving the accuracy and precision of medical operations. A few examples of existing robotic systems as disclosed by Shoham in U.S. patent publication No. 20120143084 provide means to control positioning of the surgical instrument. One computer assisted approach involves generating a mechanical constraint by a robotic arm to block movement of the instrument when the instrument is moved within or beyond a default anatomical region by the surgeon. Another approach utilizes a robotically controlled platform connected to an operating tool of the instrument to enable the operating tool to move and adjust the orientation thereof to compensate deviation of the surgeon's hand motion from the planned trajectory.

However, while the surgical instrument having a self-adjustable operating tool provides theoretically more operational flexibility over conventional instruments, maneuverability and accuracy of the instrument are not as ideal. On one hand, when operating the instrument it is difficult for the surgeon to determine the preferred range where the instrument should be placed in respect of the surgical site. In other words, without knowing the spatial range corresponding to the allowable movement of the operating tool or the capacity of the tool to compensate deviation, the surgeon can only guesstimate how far from or how close to the surgical site he/she should place the instrument. On the other hand, by not knowing the boundary of the preferred or allowable spatial range of the operating tool, the surgeon would be unaware of any unintentional deviation of the instrument from the preferred operation range.

Therefore, there is a need for a navigation system designed for the surgical instrument having a self-adjustable tool that informs the surgeon of the allowable range of the surgical instrument.

BRIEF SUMMARY OF THE DISCLOSURE

An objective of the present invention is to provide a reliable navigation system that determines the capability of the instrument to correct deviations of the operating tool real-time and presents spatial information of the surgical environment with high accuracy to the surgeon during medical operations.

Another objective of the present invention is to provide an intuitive navigation system that visualizes the capability of the instrument to correct deviations of the operating tool real-time during medical operations and offers the surgeon clear guidance on maneuvering of the surgical instrument.

An embodiment of the present disclosure provides a navigation method for a medical operation and implemented by a robotic system. The navigation method includes the steps of: (S1) receiving, at a processor of the robotic system, at least one set of navigation data, comprising steps of: receiving at least one set of registration data, receiving at least one set of instrument data, receiving at least one set of spatial sensor data, and receiving at least one set of medical operation plan data, wherein the instrument data comprises at least one set of virtual workspace or virtual active space of the robotic system, and the navigation data comprises at least one virtual object; (S2) receiving or generating, at the processor of the robotic system, at least one three-dimensional model of the virtual object in the navigation data; (S3) processing, at the processor of the robotic system, the navigation data to generate a virtual environment; (S4) processing, at the processor of the robotic system, the navigation data and the virtual environment to generate at least one navigation instruction; and (S5) presenting, at a user interface electrically connected to the robotic system, the virtual environment, the navigation instruction, or the virtual environment and the navigation instruction to a user of the robotic system for the user to refer to during the medical operation.

In a preferred embodiment, the step of (S1) further includes a step of: (S1-1) receiving at least one set of anatomical data.

In a preferred embodiment, the step of (S1-1) further comprises a step of receiving at least one set of endoscope image data from a minimally invasive image system electrically connected to the robotic system, and the step of (S5) further includes a step of: displaying the endoscope image data. The displayed endoscope image data spatially and timely coincides with the virtual anatomy in the virtual environment.

In a preferred embodiment, the virtual active space further includes a first virtual active space and a second virtual active space, and a size or a shape of the first virtual active space is different from a size or a shape of the second virtual active space.

In a preferred embodiment, the robotic system is electrically connected to an instrument system having a manipulator or a tool, the first virtual active space is associated with one of a plurality of criteria for activating the manipulator or the tool, and the second virtual active space is associated with one of a plurality of criteria for inactivating the manipulator or the tool.

In a preferred embodiment, the step of (S4) includes a step of: determining at least one spatial relationship between at least two virtual objects in the virtual environment.

In a preferred embodiment, a first virtual object of the at least two virtual objects is a virtual workspace or a virtual active space from the instrument data and a second virtual object of the at least two virtual objects is a virtual planning object from the medical operation plan data.

In a preferred embodiment, the at least one spatial relationship includes at least one compensation rating, and the compensation rating is calculated from the medical operation data and the virtual workspace or from the medical operation data and the virtual active space.

In a preferred embodiment, the step of (S4) includes a step of: processing at least one virtual planning object attribute in the medical operation plan data to generate at least one navigation instruction.

In a preferred embodiment, the navigation method further includes a step of: generating at least one set of control signal for controlling at least one function of the robotic system.

In a preferred embodiment, the control signal includes a first control signal and a second control signal, the first control signal is generated according to a first calculation result of the calculation of the navigation data, and the second navigation instruction is generated according to a second calculation result of the calculation of the navigation data.

In a preferred embodiment, the step of (S5) includes a step of: rendering three-dimensional graphics on a display device electrically connected to the processor, wherein the three-dimensional graphics includes the virtual environment, the navigation instruction, or the virtual environment and the navigation instruction.

In a preferred embodiment, a viewing angle of the rendering is aligned with an orientation of an instrument electrically connected to the robotic system.

In a preferred embodiment, the step of (S5) includes a step of: generating and displaying, by a graphical user interface (GUI) application, a plurality of two-dimensional icons according to the navigation data and the virtual environment, wherein the two-dimensional icons represent a position of an instrument electrically connected to the robotic system, an orientation of the instrument, the navigation instruction, and a range of valid orientation of the instrument.

In a preferred embodiment, the navigation instruction is presented by a light indicator or an audio device, wherein the light indicator and the audio device are electrically connected to the robotic system.

In a preferred embodiment, the navigation instruction is presented by a direction of a tool, wherein the tool is connected to a manipulator electrically connected to the robotic system.

In a preferred embodiment, the step of (S5) includes a step of: generating and displaying, by a graphical user interface (GUI) application, a plurality of two-dimensional icons according to the navigation data and the virtual environment, wherein the two-dimensional icons represent workspace progress bar.

Another embodiment of the present disclosure provides a robotic system for assisting a medical operation, comprising: a user interface; and a computer system electrically connected to the user interface, wherein the computer system includes a non-transitory computer readable medium storing a program for navigating the medical operation, the program is executable by at least one processor of the computer system and comprises instructions that, when executed by the processor, causes the robotics system to perform steps of: (S1) receiving, at a processor of the robotic system, at least one set of navigation data, including steps of: receiving at least one set of registration data, receiving at least one set of instrument data, receiving at least one set of spatial sensor data, and receiving at least one set of medical operation plan data, wherein the instrument data comprises at least one set of virtual workspace or virtual active space of the robotic system, and the navigation data comprises at least one virtual object; (S2) receiving or generating, at the processor of the robotic system, at least one three-dimensional model of the virtual object in the navigation data; (S3) processing, at the processor of the robotic system, the navigation data to generate a virtual environment; (S4) processing, at the processor of the robotic system, the navigation data and the virtual environment to generate at least one navigation instruction; and (S5) presenting, at a user interface electrically connected to the robotic system, the virtual environment, the navigation instruction, or the virtual environment and the navigation instruction to a user of the robotic system for the user to refer to during the medical operation.

In a preferred embodiment, the step of (S1) further includes a step of: (S1-1) receiving at least one set of anatomical data.

In a preferred embodiment, the step of (S1-1) further includes a step of receiving at least one set of endoscope image data from a minimally invasive image system electrically connected to the robotic system, and the step of (S5) further includes a step of: displaying the endoscope image data. The displayed endoscope image data spatially and timely coincides with the virtual anatomy in the virtual environment.

In a preferred embodiment, the virtual active space includes a first virtual active space and a second virtual active space, and a size or a shape of the first virtual active space is different from a size or a shape of the second virtual active space.

In a preferred embodiment, the robotic system is electrically connected to an instrument system having a manipulator or a tool, the first virtual active space is associated with one of a plurality of criteria for activating the manipulator or the tool, and the second virtual active space is associated with one of a plurality of criteria for inactivating the manipulator or the tool.

In a preferred embodiment, the step of (S4) includes a step of: determining at least one spatial relationship between at least two virtual objects in the virtual environment.

In a preferred embodiment, a first virtual object of the at least two virtual objects is a virtual workspace or a virtual active space from the instrument data and a second virtual object of the at least two virtual objects is a virtual planning object from the medical operation plan data.

In a preferred embodiment, the at least one spatial relationship includes at least one compensation rating, and the compensation rating is calculated from the medical operation data and the virtual workspace or from the medical operation data and the virtual active space.

In a preferred embodiment, the step of (S4) includes a step of: processing at least one virtual planning object attribute in the medical operation plan data to generate at least one navigation instruction.

In a preferred embodiment, the navigation method further includes a step of: generating at least one set of control signal for controlling at least one function of the robotic system.

In a preferred embodiment, the control signal includes a first control signal and a second control signal, the first control signal is generated according to a first calculation result of the calculation of the navigation data, and the second navigation instruction is generated according to a second calculation result of the calculation of the navigation data.

In a preferred embodiment, the step of (S5) includes a step of: rendering three-dimensional graphics on a display device electrically connected to the processor, wherein the three-dimensional graphics comprises the virtual environment, the navigation instruction, or the virtual environment and the navigation instruction.

In a preferred embodiment, a viewing angle of the rendering is aligned with an orientation of an instrument electrically connected to the robotic system.

In a preferred embodiment, the step of (S5) includes a step of: generating and displaying, by a graphical user interface (GUI) application, a plurality of two-dimensional icons according to the navigation data and the virtual environment, wherein the two-dimensional icons represent a position of an instrument electrically connected to the robotic system, the navigation instruction, and a range of valid orientation of the instrument.

In a preferred embodiment, the navigation instruction is presented by a light indicator or an audio device, wherein the light indicator and the audio device are electrically connected to the robotic system.

In a preferred embodiment, the navigation instruction is presented by a direction of a tool, wherein the tool is connected to a manipulator electrically connected to the robotic system.

In a preferred embodiment, the step of (S5) includes a step of: generating and displaying, by a graphical user interface (GUI) application, a plurality of two-dimensional icons according to the navigation data and the virtual environment, wherein the two-dimensional icons represent workspace progress bar.

In a preferred embodiment, the system further comprising an instrument system comprising a tool and a manipulator connected to the tool, and the instrument system is electrically connected to the computer system.

In sum, according to the various embodiments of the present disclosure, the robotic system utilizes data regarding the workspace of the manipulator of the instrument to provide navigation instructions to a user of the robotic system. By referencing to the navigation instructions, the user is provided a sense of the capability of the instrument to correct deviations of the position or orientation of the tool from a predetermined medical operation plan, according to the position and/or orientation of the instrument. Further, the navigation instructions also inform the user of the suggestions on how to manually manipulate the instrument to an optimal position or orientation to improve the capability of the instrument to correct the deviations of the position or orientation of the tool from the predetermined medical operation plan, according to the position and/or orientation of the instrument.

BRIEF DESCRIPTION OF THE DRAWINGS

The accompanying drawings illustrate one or more embodiments of the present disclosure and, together with the written description, explain the principles of the present disclosure. Wherever possible, the same reference numbers are used throughout the drawings to refer to the same or like elements of an embodiment.

In accordance with common practice, the various described features are not drawn to scale and are drawn to emphasize features relevant to the present disclosure. Like reference characters denote like elements throughout the figures and text.

DETAILED DESCRIPTION OF THE PREFERRED EMBODIMENT

Figure 1:
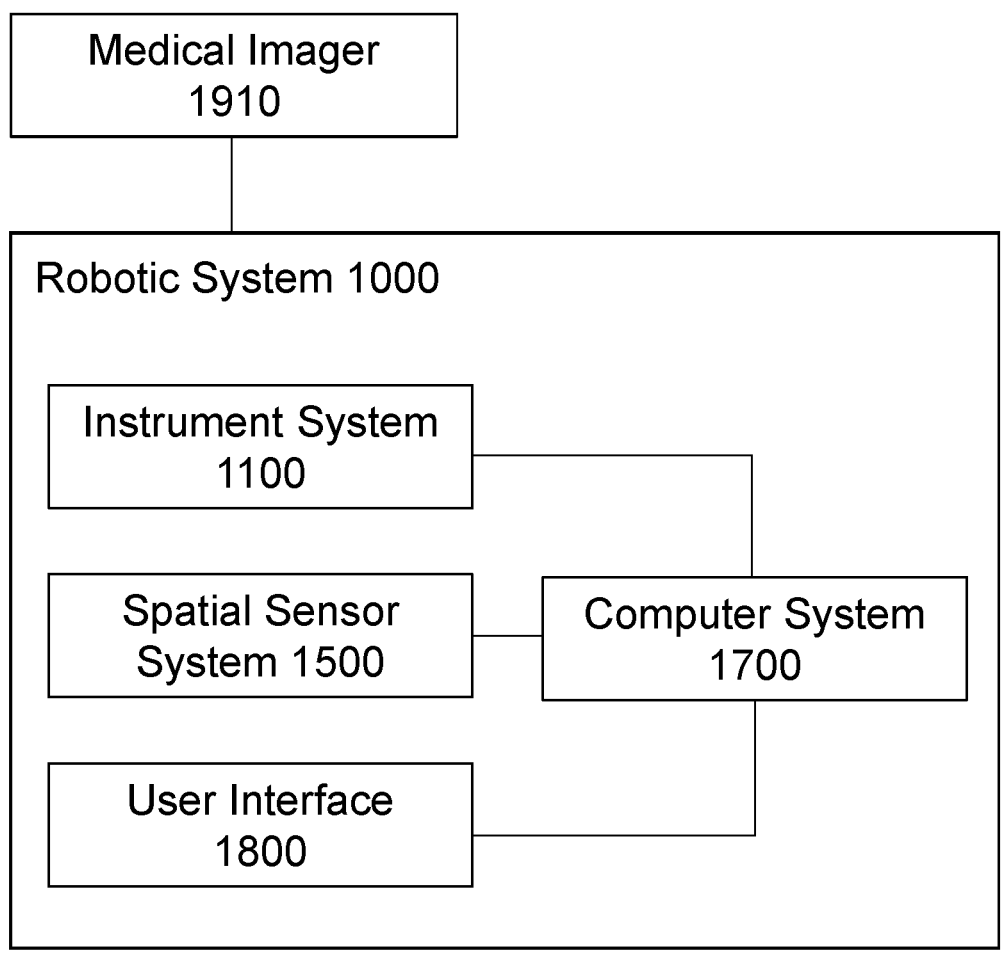
FIG. 1 is a block diagram of a robotic system in accordance with an embodiment of the present disclosure.

The present disclosure will now be described more fully hereinafter with reference to the accompanying drawings illustrating various exemplary embodiments of the disclosure. The present disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

It will be understood that the terms "and/or" and "at least one" include any and all combinations of one or more of the associated listed items. It will also be understood that, although the terms first, second, third etc. may be used herein to describe various elements, components, regions, parts and/or sections, these elements, components, regions, parts and/or sections should not be limited by these terms. These terms are only used to distinguish one element, component, region, part or section from another element, component, region, layer or section. Thus, a first element, component, region, part or section discussed below could be termed a second element, component, region, layer or section without departing from the teachings of the present disclosure.

The term "medical operation" used herein refers to a procedure or part of the procedure that applied on a patient for a specific medical purpose. For example, a medical operation may be a computer assisted surgery, or the medical operation may be a registration process which is a part of a computer assisted surgery.

The term "virtual object" used herein refers to a set of computer-executable data that can be stored in a storage medium. A virtual object may include a representation/simulation of a real-world object or a geometric concept.

The term "object property" used herein refers to the at least one attributes of the virtual object. In other words, object properties are contents of the virtual object encoded in the data files and stored in a data structure or memory configuration.

The term "virtual environment" used herein refers to a set of data include a representation/simulation of a real-world environment. A virtual environment includes at least one well defined coordinate system and at least one virtual object. Spatial properties in respective to the well-defined coordinate system of the at least one virtual object are also well-defined.

The term "spatial property" used herein refers to position/orientation of an object. The term "spatial relationship" used herein refers to relative position or relative orientation between two objects.

In the present disclosure, exemplary descriptions of the data structure are for the purpose of explaining data attributes. In other words, the necessary content encoded in the data and corresponded processing steps are explained in the exemplary descriptions. It will be understood that these exemplary descriptions should not limit the data structure, storage method, reading method, processing method, measuring method and describing method of these necessary content encoded in the data. It will also be understood that these exemplary descriptions should not limit the programming method or programming language of the corresponded processing program, computing program, measuring program or other application.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 2:
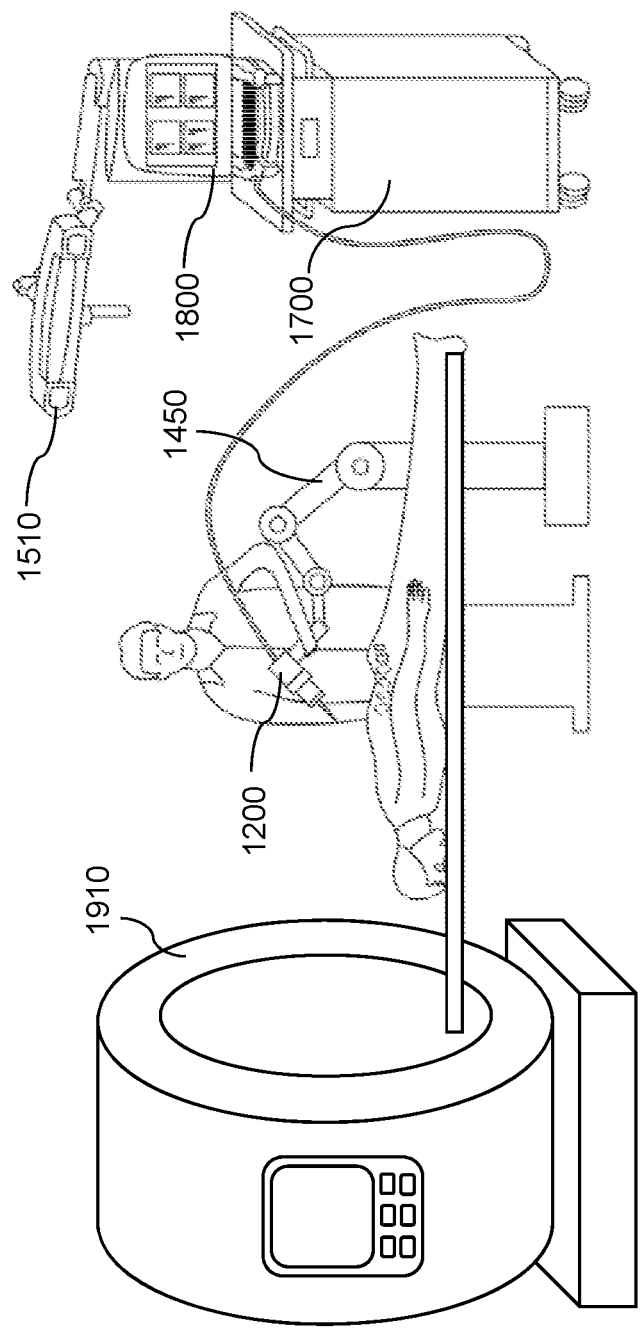
FIG. 2 is a schematic illustration of the robotic system in accordance with an embodiment of the present disclosure.

Referring now to FIG. 1 and FIG. 2. According to an embodiment of the present disclosure, a robotic system 1000 for pre-surgical and surgical operations includes surgical hardware coupled with electronic modules and processor-executable instructions. The robotic system 1000 includes an instrument system 1100, a spatial sensor system 1500, a user interface 1800, and a computer system 1700 electrically connected to the instrument system 1100, the spatial sensor system 1500, and the user interface 1800. In the embodiment, the robotic system 1000 allows a user (e.g., a surgeon) to conduct surgery on a subject (e.g., a patient) by the instrument system 1100 with reference to the user interface 1800. At least one medical imager 1910 is in communication with the robotic system 1000 and is configured to acquire medical images of the subject and transmit the images to the robotic system 1000. The spatial sensor system 1500 is configured to generate spatial information of the subject and the environment. The computer system 1700 is configured to generate a virtual anatomical model according to the medical images and a surgical plan according to the virtual anatomical model, to track the surgical environment according to the spatial information received from the spatial sensor system 1500, and to control movement or alter the kinematic state of the manipulator 1210. The user interface 1800 visualizes the anatomical model and allows the user to navigate through the operating field according to the surgical plan.

As illustrated in FIG. 2, the instrument system 1100 of the robotic system 1000 includes a hand-held instrument 1200 for performing surgery on the subject. In the embodiment, the instrument system 1100 may further include a support arm 1450 connected to the hand-held instrument 1200 to reduce weight load on the hands of the user and optionally provide more operational stability during surgeries.

Figure 3:
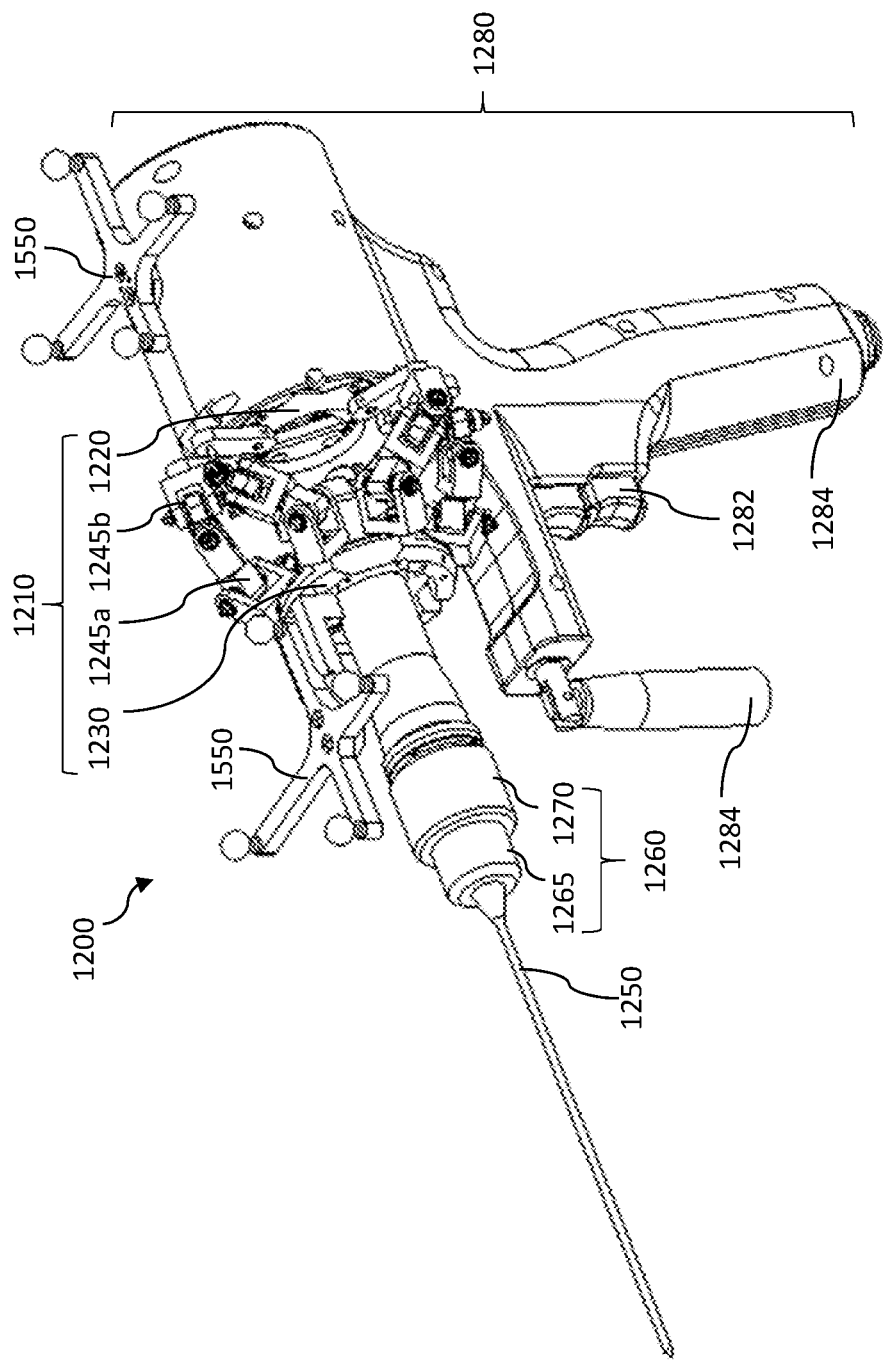
FIG. 3 is a perspective view of a hand-held instrument of the robotic system in accordance with an embodiment of the present disclosure.
Figure 4:
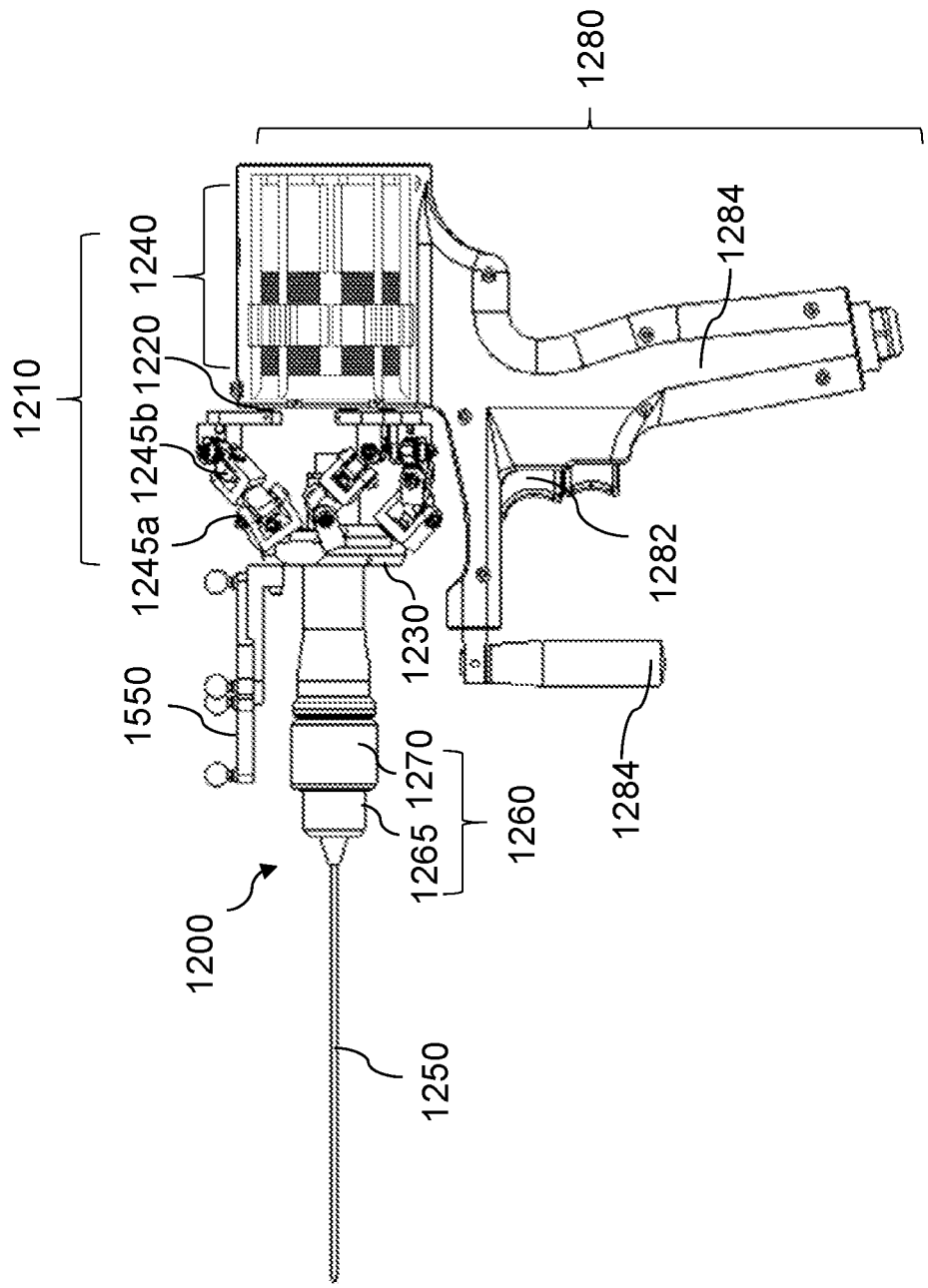
FIG. 4 is a side view of the hand-held instrument of the robotic system in accordance with an embodiment of the present disclosure.

Referring to FIG. 3 and FIG. 4. According to an embodiment, the hand-held instrument 1200 includes a tool 1250, a tool installation base 1260, a manipulator 1210, and an instrument housing 1280. The tool 1250 is configured to contact or modify an anatomical surface on a body part of the subject. The tool installation base 1260 is connected to an end of the tool 1250 and the manipulator 1210 so that the tool 1250 is stably connected to the manipulator 1210. The manipulator 1210 is a mechanism controlled by the computer system 1700 for manipulating the position and orientation of the tool 1250. The instrument housing 1280 is connected to the manipulator 1210 to accommodate at least a portion of the manipulator 1210 and provide one or more handles 1284 for allowing the user to hold onto and maneuver the instrument 1200 during operation of the robotic system 1000.

In the embodiment, the tool 1250 may be a probe or indicator for contacting or assessing an anatomical site of the subject and detecting the structure or status of the anatomical site. The tool 1250 may be a drill bit, bur, curette, saw, screwdriver or other tool commonly used in surgical medicine that modifies or removes a portion of the tissues at the anatomical site by drilling, milling, cutting or scraping. In some embodiments, the tool 1250 is a mechanical, optical or ultrasound probe for performing surface matching registration and may be, but is not limited to, a rigid probe, a pressure sensor, a piezoelectric sensor, an elastomeric sensor, an optical camera, a laser scanner or an ultrasonic scanner.

Figure 5:
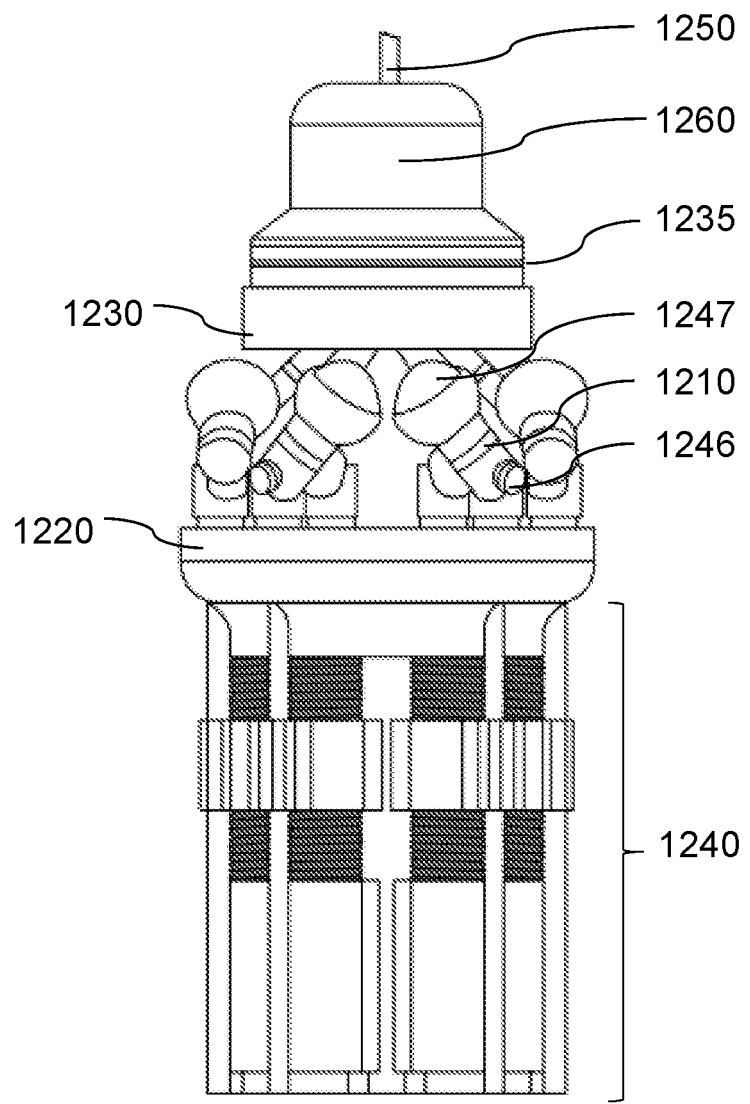
FIG. 5 is a side view of a manipulator of the hand-held instrument of the robotic system in accordance with an embodiment of the present disclosure.
Figure 6:
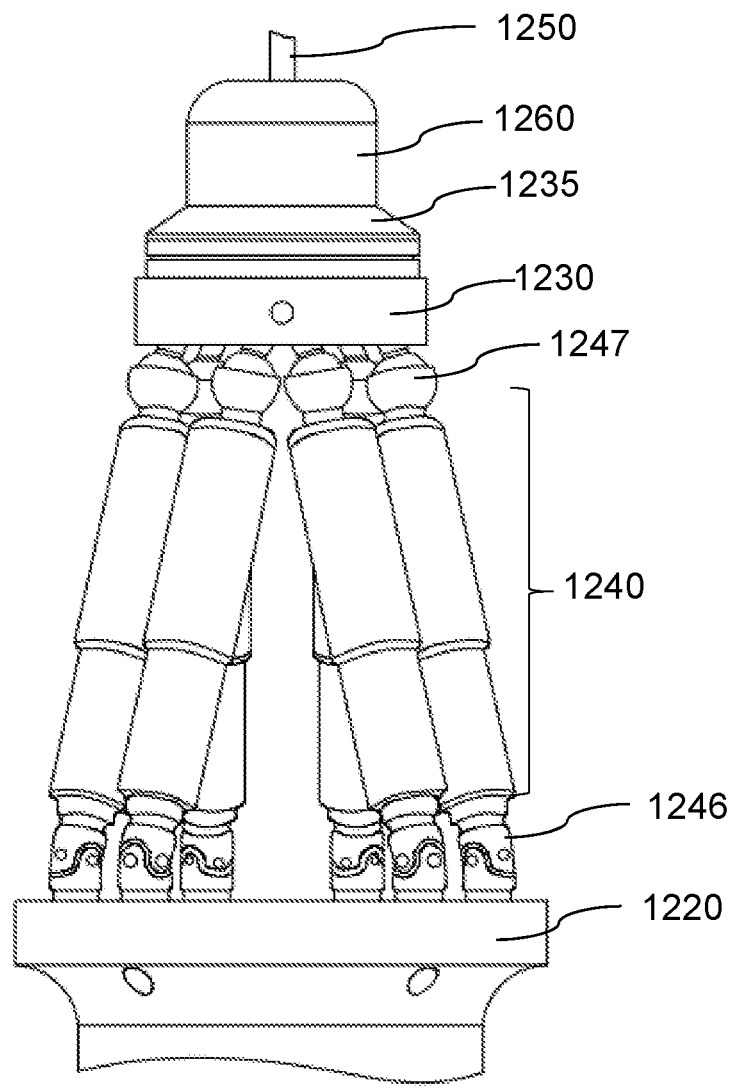
FIG. 6 is a side view of another manipulator of the hand-held instrument of the robotic system in accordance with an embodiment of the present disclosure.

In the embodiment, the tool installation base 1260 is connected to the tool 1250 and a first side of a robotically controlled platform 1230 of the manipulator 1210. The tool installation base 1260 includes a tool adaptor 1265 and a motor 1270 connected to the tool adaptor 1265. The tool adaptor 1265 may be a clamp or other fastening structure for holding an end of the tool 1250 firmly to avoid displacement of the tool during operations. The motor 1270 may be a direct current (DC) motor or an alternating current (AC) motor for transducing electric energy into mechanical energy and generating a linear or rotary force to drive movement of the tool 1250. In an alternative embodiment, the motor may be disposed at the rear end of the instrument to reduce loading on the manipulator 1210 during operation of the instrument and to redistribute the weight of the instrument 1200 for improved user ergonomics. Additionally, as illustrated in FIG. 5 and FIG. 6, the tool installation base 1260 may further include a force sensor 1235 connected to the first side of the platform 1230 for detecting the force and/or torque sustained by the tool 1250 during surgeries. In other embodiments, the force sensor 1235 may be disposed in the probe or tool of the instrument; alternatively, the instrument 1200 may further include another force sensor (not shown in figures) disposed in the probe or tool. The force sensor may be, but is not limited to, a strain gauge, a force-sensitive resistor, a pressure transducer, a piezoelectric sensor, an electroactive polymer or an optical fiber bending sensor.

In the embodiment, the manipulator 1210 includes a base 1220, the platform 1230 connected to the tool installation base 1260, a plurality of joints 1245a, 1245b mounted on a second side of the platform 1230 away from the tool 1250 and on a first side of the base 1220 facing the platform 1230, and a plurality of actuators 1240 connected to the base 1220 on a second side of the base 1220 away from the platform 1230. As illustrated in FIG. 4, the base 1220 may be immobilized on or accommodated in the instrument housing 1280. The manipulator 1210 may be a parallel manipulator, such as a Stewart manipulator with six degrees of freedom (DOFs), for higher space efficiency and maneuverability. Additionally, the manipulator is preferably made of stainless steel or carbon fiber and arranged in a specific mechanical structure that allows the manipulator 1210 to possess sufficient sustainability against the force and/or torque generated from the tool 1250 contacting the subject during surgeries.

In the embodiment, the joints of the manipulator 1210 may be, but are not limited to, revolute joints, prismatic joints, spherical joints, universal joints, cylinder joint, or any combination thereof that enables a desired DOF. As exemplified in FIG. 5 and FIG. 6, the manipulator 1210 having a general Stewart platform with six DOFs may include universal joints 1246 and spherical joints 1247 to enable broad ranges of motion and various kinematic states of the manipulator 1210. The manipulator 1210 may further include a plurality of connectors, each being connected to one of the joints 1245a and one of the joints 1245b, to enable a broader range of movement of the tool 1250.

In the embodiment, the actuators 1240 of the manipulator 1210 connected to the base 1220 on the side opposite to the joints are configured to drive the joints, and the connectors if any, to move according to control signals transmitted from the computer system 1700. In an alternative embodiment, the actuators 1240 and the joints may be disposed on the same side of the base 1220. As exemplified in FIG. 6, the actuators 1240 are disposed between the base 1220 and the platform 1230, with each of the actuators 1240 being joined by a universal joint 1246 and a spherical joint 1247. The plurality of actuators 1240 may be linear actuators for higher precision and stronger sustainability.

Referring again to FIG. 3 and FIG. 4. In the embodiment, in addition to accommodating the manipulator 1210 and providing handles 1284, the instrument housing 1280 may further include a control module 1282 for allowing the user to trigger, halt, or adjust actions of the tool 1250 or perform other functions of the instrument 1200.

In the embodiment, the hand-held instrument 1200 may be used with a calibration device configured to calibrate kinematic state of the manipulator 1210 in respect of the instrument housing 1280 so as to ensure geometric accuracy of the instrument 1200.

Figure 7:
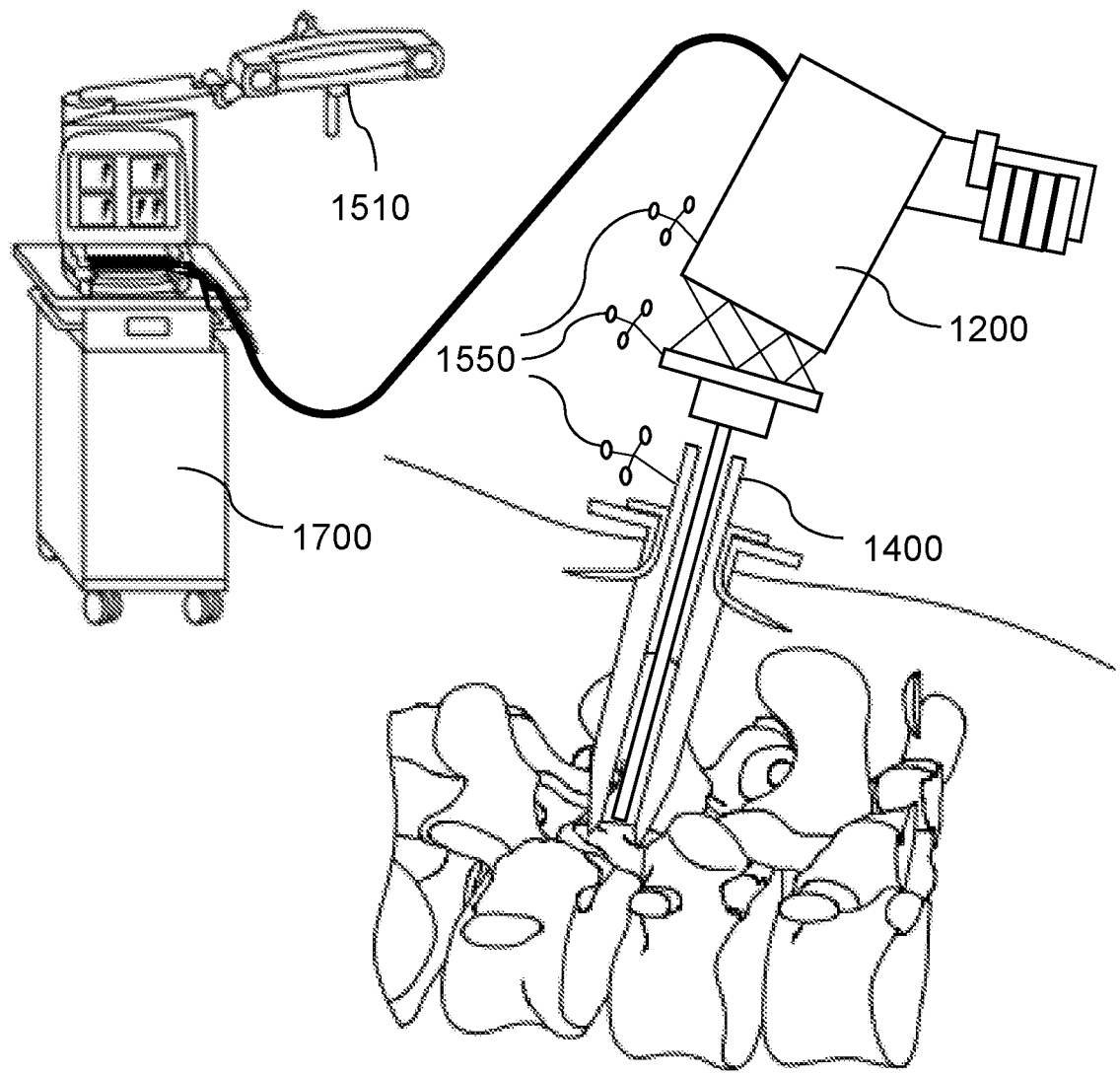
FIG. 7 is a schematic illustration of an operation state of the robotic system in accordance with an embodiment of the present disclosure.

Referring to FIG. 7. The instrument 1200 may be used with a trocar 1400, especially in a minimally invasive surgery, to provide a physical portal for the tool 1250 of the instrument 1200 to reach the anatomical site of interest. In an alternative embodiment, the trocar 1400 may be removably connected to the platform 1230 of the manipulator 1210 to enable simultaneous entry of the trocar 1400 and the tool 1250 into the anatomical site.

Figure 8:
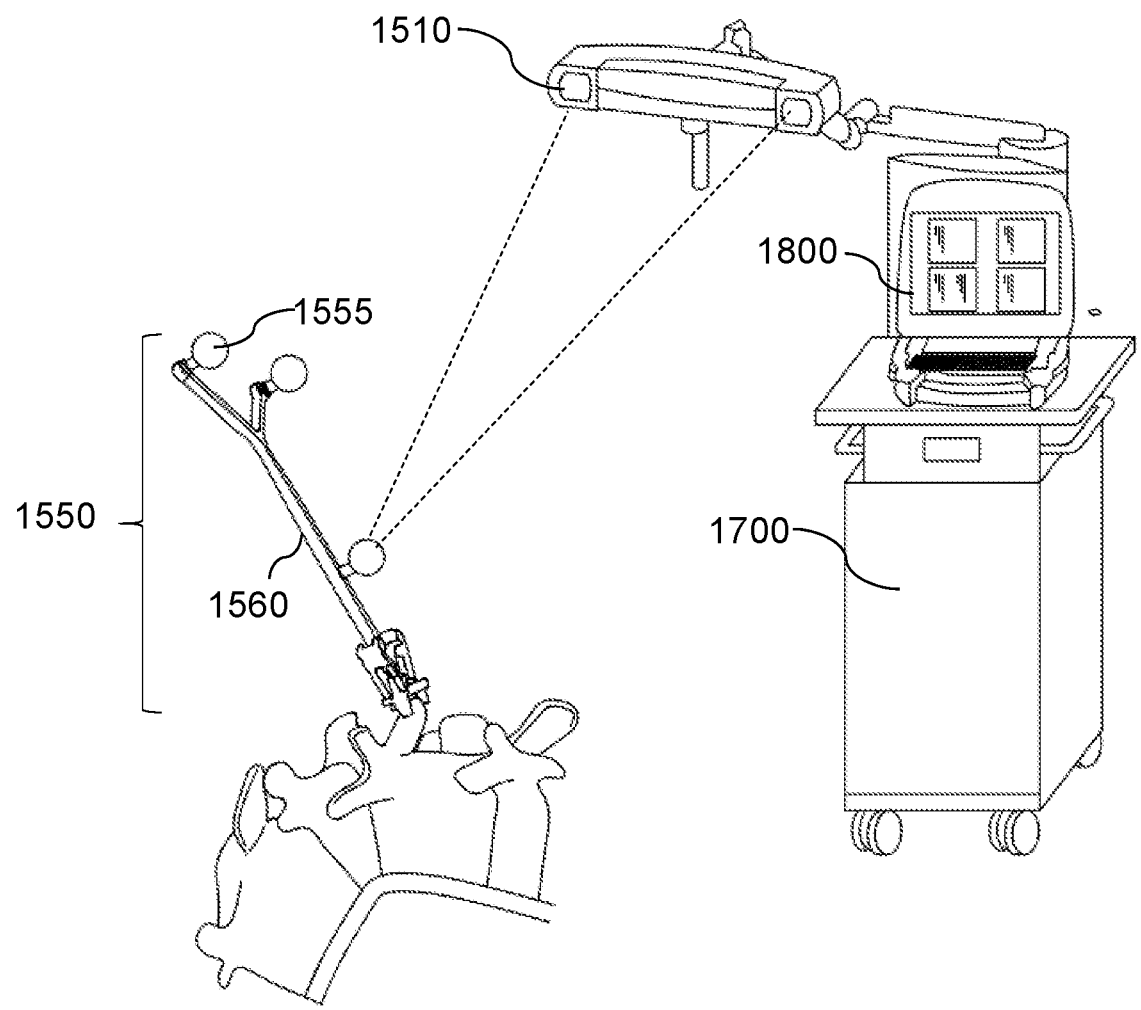
FIG. 8 is a schematic illustration of an operation state of a spatial sensor system of the robotic system in accordance with an embodiment of the present disclosure.

Referring now to FIG. 8. According to an embodiment of the present disclosure, the spatial sensor system 1500 of the robotic system 1000 is configured to detect and thus enable tracking of the spatial information (e.g., location and orientation) of at least one target object, and includes at least one spatial marker frame 1550 removably attached to the target object, and a spatial sensor 1510 having at least one camera for receiving signals transmitted from the spatial marker frame 1550.

As exemplified in FIG. 7 and FIG. 8, the target object may be the instrument 1200, the trocar 1400, or a selected anatomical site. In the embodiment, the spatial marker frame 1550 includes a plurality of markers 1555 for emitting electromagnetic signals, sound wave, heat, or other perceivable signals, and an adaptor 1560 removably attached to the target object for holding the markers 1555 so that the target object becomes trackable by the spatial sensor 1510. In another embodiment, the spatial sensor system 1500 may further include a signal generator (not shown in figure) disposed on the spatial sensor 1510 or at a predefined location. Consequently, signal transmission by the markers 1555 may be active or passive; in other words, the signals emitted by the markers 1555 may be generated by the marker spheres, or the markers 1555 may be covered with reflective material so that signals generated by the signal generator are reflected by the markers 1555 to the spatial sensor 1510.

In the embodiment, the signal received by the spatial sensor 1510 is transmitted to the computer system 1700 as spatial information of the target object. Further, the markers 1555 of the spatial marker frame 1550 may be arranged on the adaptor 1560 in a specific pattern, as exemplified in FIG. 8, thus allowing the computer system 1700 to generate orientation information of the target object accordingly. The computer system 1700 may generate control signals according to the spatial and orientation information to control movement or alter kinematic state of the manipulator 1210 of the instrument 1200 or generate instructions to be shown on the user interface 1800 to prompt the user to move the instrument 1200 to a designated location or orientation.

According to an embodiment of the present disclosure, the computer system 1700 of the robotic system 1000 includes a processor 1710 and a storage unit. The processor 1710 may be a general purpose processor, an application-specific instruction set processor or an application-specific integrated circuits that performs operations on a data source, such as the storage unit or other data stream. For example, the processor is an ARM based processor or an 8086x processor. In some embodiments, the processor 1710 further includes a plurality of digital or analog input/output, and may be a real-time operating system (RTOS) processor. The storage unit may store digital data assigned by the processor for immediate use in the computer system. The storage unit may be volatile, such as flash memory, read-only memory (ROM), programmable read-only memory (PROM), and erasable programmable read-only memory (EPROM), or non-volatile, such as dynamic random access memory (DRAM) and static random access memory (SRAM).

According to an embodiment, the user interface 1800 includes at least one output device for presenting information to the user and at least one input device. The information presented by the user interface 1800 may include, but is not limited to, surgical plans, two-dimensional (2D) or 3D reconstruction images, 2D or 3D drilling status (e.g., position, angle, depth or bending of the tool), compensation range of the tool, user guidance, warning area, notification of tool deviation from the surgical plan and notification of force sustainability limit of the tool. The output device may be a display, a light indicator or other visual means; alternatively, the output device may also be, or further include, a speech synthesizer or other audio means. The input device is capable of transducing commands entered by the user into electrical signals, and may be a pedal, a keyboard, a mouse, a touch panel, a voice recognition interface, or a gesture recognition interface.

According to an embodiment, the robotic system 1000 may further include a minimally invasive image sensor system. The minimally invasive image sensor system is configured to sense, process, and output optical images of an anatomical site of the patient. The minimally invasive image sensor system may include an endoscope device 4110, an endoscope image processor and other accessories, such as but not limited to an endoscope holder, an endoscope introducer, and an endoscope position detection unit.

The minimally invasive image sensor system is electrically connected to the processor 1710 for exchange of data. The position and orientation of the endoscope device 4110 may be tracked by the spatial sensor system 1500.

In some embodiments, the endoscope device 4110 may be mechanically coupled to the manipulator 1210 of the instrument 1200. In the embodiments, the position and orientation of the endoscope device is controlled by the manipulator 1210.

In some embodiments, the endoscope device 4110 may be mechanically coupled to the instrument 1200 so that the endoscope device has a camera angle parallel to the longitudinal axis of the instrument (i.e., the rotation axis of the tool when the manipulator is in an initial posture or initial kinematic state).

Figure 9:
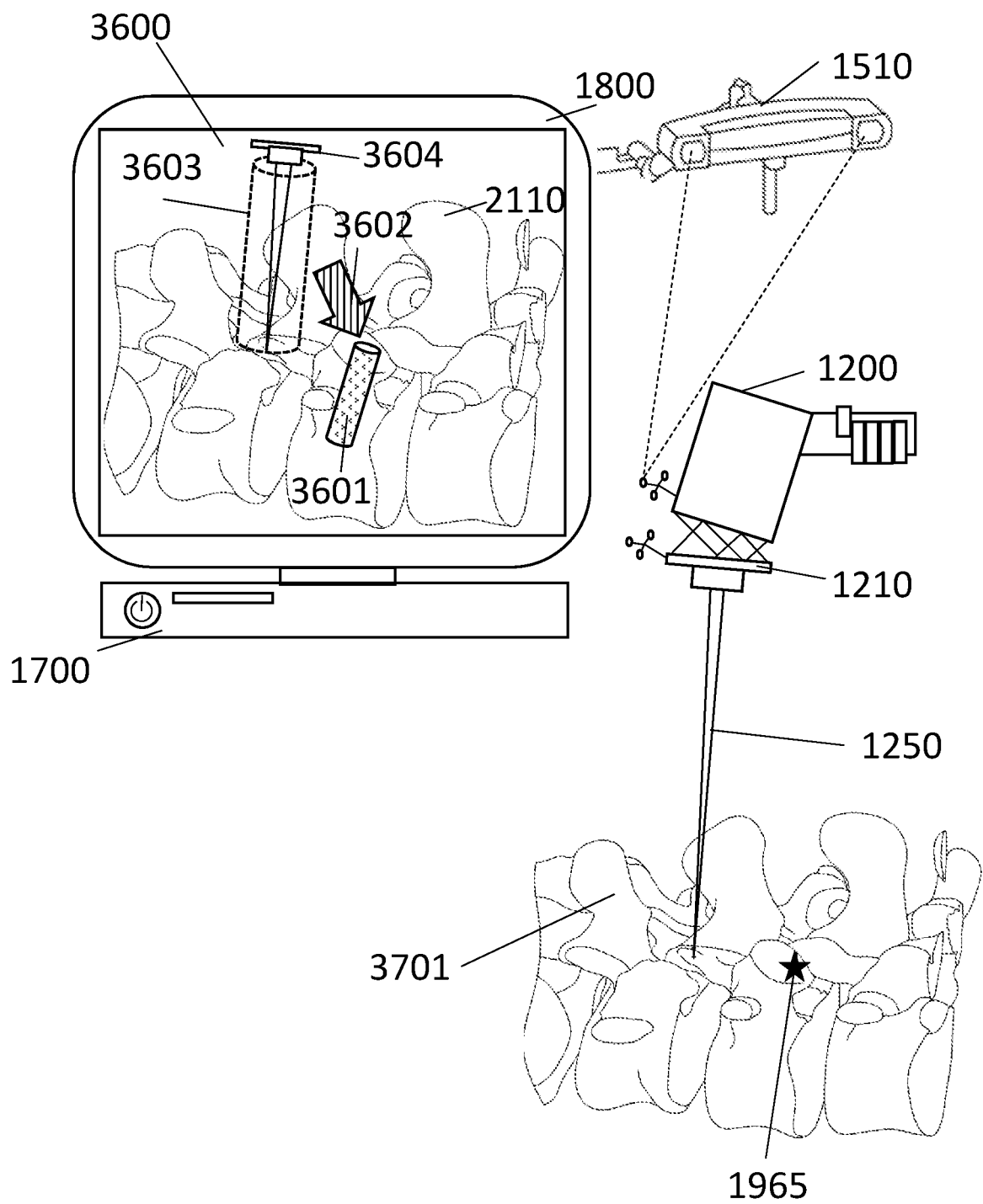
FIG. 9 is a schematic illustration of an operation state of the robotic system in accordance with an embodiment of the present disclosure.

Referring to FIG. 9. The user interface 1800 may also present computer generated navigation instructions and/or a computer generated virtual environment 3600 to the user (e.g., a surgeon), so as to facilitate manipulation of the instrument 1200.

The virtual environment 3600 includes a well-defined coordinate system and at least one virtual object. In an embodiment, the virtual object may include a virtual instrument 3604, a virtual anatomy 2110, a virtual medical operation plan 3601, and a virtual workspace 3603 of the manipulator 1210 of the instrument 1200. In the virtual environment 3600, spatial relationships between each of the virtual objects and the well-defined coordinate system are well-defined to simulate a real-world surgical environment. In order to define the spatial relationships among the virtual objects, the spatial sensor system 1500 is configured to provide spatial properties of real-world objects to the computer system 1700. The spatial properties may be position or orientation.

By referencing the presented navigation instructions and spatial relationships among the virtual objects in the virtual environment, the user may easily comprehend the complex relationship between the state of the manipulator 1210 and the spatial properties of the virtual objects.

As exemplified in FIG. 9, the virtual environment 3600 includes a virtual medical operation plan 3601 corresponding to a target spot of operation 1965. The target spot 1965 is effected by the tool 1250 of the instrument 1200. By referencing to the position/orientation of the virtual workspace 3603 and the virtual medical operation plan 3601, the user may position the instrument 1200 within a spatial range where the tool 1250 can reach the target spot 1965 on the anatomical site 3701. Additionally, the user interface 1800 may also present a navigation instruction 3602 to inform the user of a movement suggestion, such as a suggested direction of movement of the tool 1250.

Figure 10:
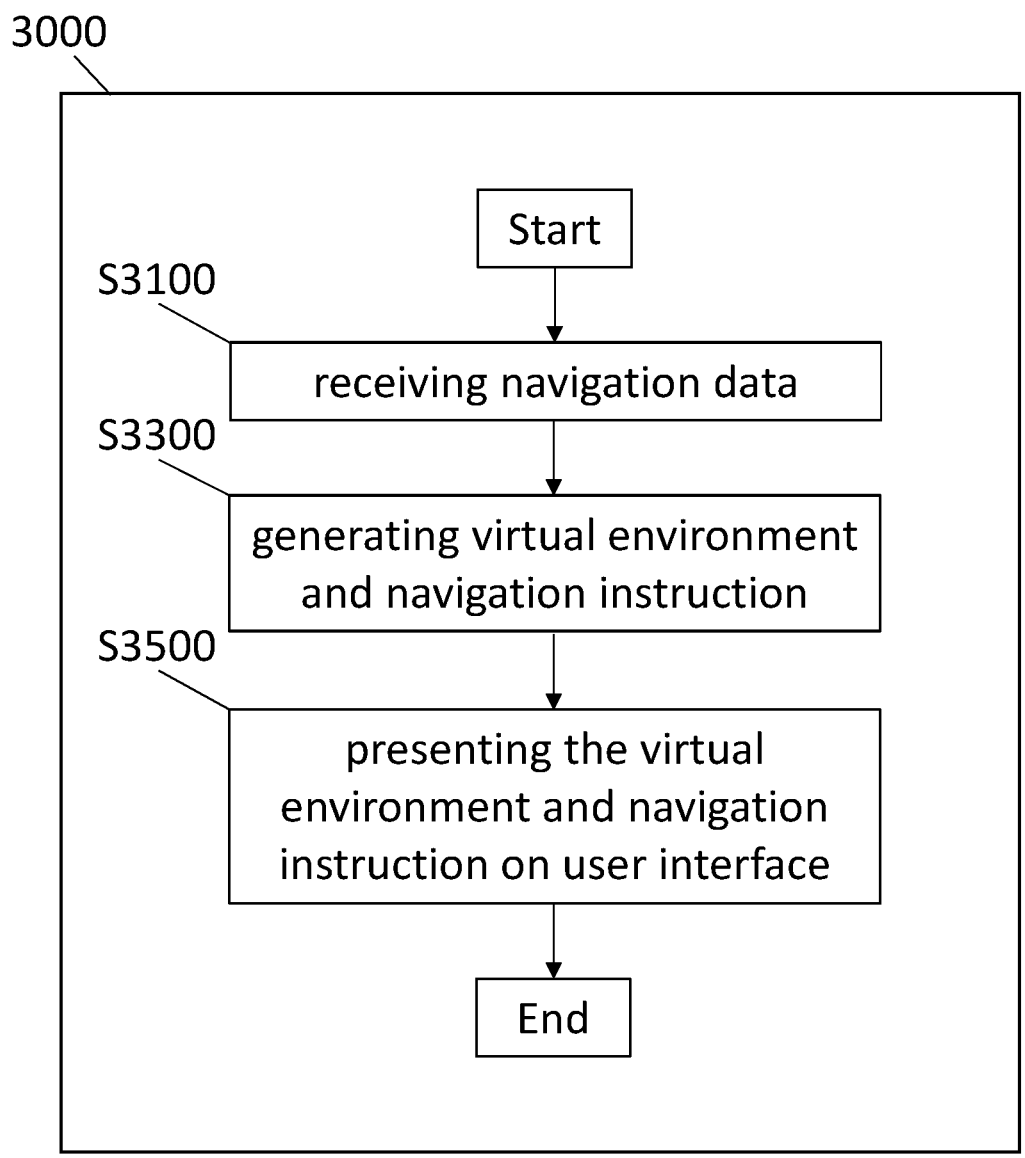
FIG. 10 is a flow diagram of a navigation method of the robotic system in accordance with an embodiment of the present disclosure.

Referring to FIG. 10, a flow diagram of a navigation method 3000 for assisting medical operations in accordance with an embodiment of the present disclosure is provided. In the embodiment, the navigation method 3000 performed by the robotic system 1000 includes the steps of: (S3100) receiving navigation data from a variety of data sources; (S3300) generating the virtual environment 3600 and the navigation instruction 3602; and (S3500) presenting the virtual environment 3600 and navigation instruction 3602 on the user interface 1800. The navigation method 3000 allows the user to perform medical operations on a subject by using the instrument system 1100 with reference to the virtual environment 3600 and the navigation instruction 3602 on the user interface 1800.

In some embodiments, the navigation method 3000 may be repeatedly performed. In other embodiments, the orders of the steps S3110, S3300, S3500 of the navigation method 3000 may be altered. For example, during the medical operation (e.g., a surgery), in order to provide the real-time position/orientation of the patient and the instrument to the surgeon(s), the navigation method 3000 may update the position/orientation of the patient/instrument by repeatedly performing Steps S3100, S3300, and S3500.

In Step S3100, the processor 1710 receives the navigation data from various data sources. The navigation data may include a variety of virtual objects. Each of the virtual objects may include a set of object properties. For example, the set of object properties may include identity, spatial properties, or shape.

The identity of a virtual object corresponds to a real object that the virtual object represents. For example, a virtual object, which includes the identity of an instrument 1200, is configured to represent the instrument 1200. The identity of a virtual object may correspond to a geometric concept that the virtual object represents, and the geometric concept may be used to generate a computer graphics or to calculate spatial relationships. For example, the identity of a virtual object may correspond to a workspace of the instrument 1200. For another example, the identity of a virtual object may correspond to a desired trajectory of the instrument 1200.

The spatial properties of a virtual object may include position, orientation or size of the virtual object. For every virtual object, spatial properties may be a relative value in respective to a reference coordinate system.

The shape of a virtual object describes the geometric boundary of the virtual object. The shape of a virtual object is used to form the three-dimensional model. The shape may be configured in a variety of three-dimensional modeling data structures, such as point cloud, wire-frame model, boundary representation, space partitioning tree, or others.

In an embodiment, the navigation data may be image data that is/are compatible to the standards of Digital Imaging and Communication in Medicine (DICOM) or other medical image standards. In another embodiment, the navigation data may be a vector representing the orientation of an object, a set of image data in the form of matrix, or a quaternion number representing position and orientation of the object.

Figure 11:
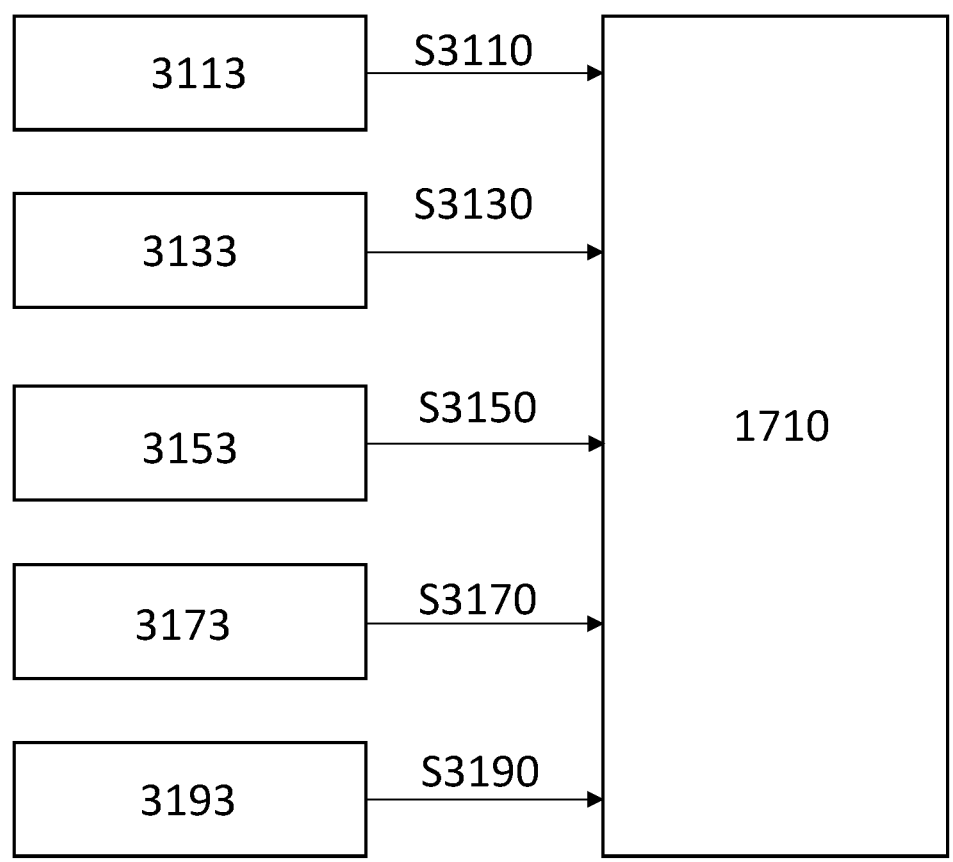
FIG. 11 is a block diagram showing the steps of receiving navigation data in the navigation method in accordance with an embodiment of the present disclosure.

Referring to FIG. 11. According to an embodiment, the step of receiving navigation data (S3100) may include the steps of: (S3110) receiving anatomical data; (S3130) receiving instrument data; (S3150) receiving spatial sensor data; (S3170) receiving registration data; and (S3190) receiving medical operation plan data. It is to be understood that the steps of S3110, S3130, S3150, S3170, S3190 are presented herein without particular order; in other words, the steps may be performed separately, simultaneously, or sequentially in a specific order.

In Step S3110, the processor 1710 receives a least one sets of anatomical data from an anatomical data source 3113. The anatomical data source 3113 may be the storage unit of the robotic system 1000, other external memory device or other external processing device. The anatomical data may include a virtual object for representing an anatomical site 3701 (e.g. spine of a patient). The virtual object in the anatomical data may include object properties, such as identity, size, shape, mechanical features or physiological features of the anatomical site 3701. In this disclosure, the term "virtual anatomy" refers to a virtual object for representing an anatomical site. The virtual anatomy includes the identity of the anatomical site. The anatomical data may be generated in a pre-operatively or intra-operatively. For example, the anatomical data may be pre-operative or intra-operative medical tomographic images of the anatomical site, such as computed tomographic (CT) images of the spine, magnetic resonance images (MM) of the brain, or ultrasound images of the muscles.

According to an embodiment of the present disclosure, the anatomical data may include endoscope image data (i.e., image data and/or video data outputted by the minimally invasive image sensor system. For example, the anatomical data may be video data of a spine of the patient acquired by the endoscope device 4110.

In Step S3130, the processor 1710 receives a least one sets of instrument data from an instrument data source 3133. The instrument data source 3133 may be the storage unit of the robotic system 1000, other external memory device or other external processing device. The instrument data may include at least one virtual object that represents the instrument system 1100 or components of the instrument system 1100. In this disclosure, the term "instrumental virtual object" refers to virtual objects in the instrument data. An instrumental virtual object may include object properties such as identity, size, shape, mechanical features of the instrument system 1100.

As illustrated in FIGS. 2-6, the identity of an instrumental virtual object may include the instrument 1200, the manipulator 1210, the base 1220, the platform 1230, the actuator 1240, the joint 1245, the tool 1250, the probe, the tool installation base 1260, the tool adaptor 1265, the motor 1270, the instrument housing 1280, the calibration device, the tool guide 1310, the manipulator guide 1320, the charging module 1330, the base 1340 of the calibration device, the trocar 1400, the hanging arm 1450, the spatial sensor 1510, the spatial marker 1550, the markers 1555, an implant, and the endoscope device 4110. The identity of instrumental virtual object may also be a workspace of the manipulator 1210 of the instrument 1200, and an active space of the instrument 1200.

In the present disclosure, the term "virtual workspace" refers to a virtual object for representing a workspace. The workspace of the manipulator 1210 of the instrument 1200 is the set of all reachable points of the end-effector (e.g., the tool 1250) when the base of the manipulator 1200 is remained static. In an embodiment, the workspace of the manipulator 1210 is the set of all reachable points of the tool 1250 (e.g. the reachable point of the tip of a drill bit). Furthermore, the shape and size of the workspace of the manipulator 1210 may vary by the number of degree of freedom (DOF) of the manipulator. For example, the workspace of a manipulator with six DOF may be a three-dimensional shaped volume. For another example, the workspace of a manipulator with only one DOF may be a point, an one-dimensional curve, or an one-dimensional straight line.

A virtual workspace may include object properties corresponding to a workspace of the instrument 1200. For example, the object properties may include identity for representing a specific workspace, shape/size of the workspace, and spatial properties of the workspace.

The active space of the manipulator 1210 of the instrument 1200 may be a subset of the workspace. In other words, the active space is a part of the set of all reachable points of the end-effector when the base of the manipulator 1210 is remained static. In this disclosure, the term "virtual active space" refers to a virtual object for representing an active space. A virtual active space include identity of an active space.

The virtual workspace (or the virtual active space) may interact with other virtual objects. The interaction of the virtual workspace 3603 (or a virtual active space) with other virtual objects may be defined by calculating their spatial relationships. Based on the interaction of the virtual workspace 3603 (or the virtual active space) with other virtual objects, the processor 1710 may generate control signal for controlling the robotic system 1000. For example, the function of robotic manipulation of the instrument 1200 may be activated when a virtual workspace 3603 (or a virtual active space) includes another virtual object. For another example, a virtual workspace 3603 (or a virtual active space) having another virtual object may be set as one of the criteria for activating the function of robotic manipulation of the instrument 1200.

Alternatively, the function of robotic manipulation of the instrument 1200 may be inactivated when a virtual workspace 3603 (or a virtual active space) space does not include a target virtual object. For another example, a virtual workspace 3603 (or a virtual active space) without the target virtual object may be set as a criteria for inactivating the function of robotic manipulation of the instrument 1200.

The size, shape, and mechanical features of the instrumental virtual objects may correspond to the identity of the instrumental virtual object. For example, an instrumental virtual object representing a specific instrument may include the size attribute and the shape attribute of that specific instrument. For example, the instrument data may include a series of computer generated design diagram of the manipulator 1210.

In one embodiment, the active space may be defined by a user of the robotic system 1000. In another embodiment, the active space may include a first active space and a second active space. The first active space is configured to set a first criteria for activating/turning on at least one function of the manipulator. The second active space is configured to set a second criteria for inactivating/turning off at least on function of the manipulator. The shape of the first active space and the second active space may be identical or different.

The instrument data may be encoded in and stored as a variety of computer file formats. For example, instrumental virtual objects may be Computer-Aided Design (CAD) files that includes the shape, size and other object properties.

Referring again to FIG. 11. In the step of S3150, the processor 1710 receives at least one set of spatial sensor data from a spatial sensor data source 3153. The spatial sensor data source 3153 may be the spatial sensor system 1500, the storage unit of the robotic system 1000, other external memory device or other external processing device. The spatial sensor data may include virtual objects for representing the spatial markers. In this disclosure, the term "virtual spatial marker" refers to a virtual object for representing a spatial marker.

Virtual spatial markers may include object properties such as identity, shape, size and spatial properties. The identity of a virtual spatial sensor may be at least one spatial marker. The spatial properties may be position and orientation. The position and orientation may be represented by a variety of data structures, such as an one-dimensional array or two-dimensional array. The shape of a virtual spatial sensor may represent the shape of the spatial marker. Therefore, in an example, the spatial sensor data may be a two-dimensional array for representing a quaternion number that includes position and orientation of an object.

In Step S3170, the processor 1710 receives a least one set of registration data from a registration data source 3173. The registration data source 3173 may be the storage unit of the robotic system 1000, other external memory device or other external processing device. The registration data are configured to define transformation relationships between at least two distinct coordinate systems. Registration data may include spatial properties of an reference point in respect to two or more distinct coordinate systems. For example, by defining the coordinate of a reference point in two distinct coordinate systems, a transformation matrix between the two coordinates may be derived. By introducing a registration data, spatial properties of a virtual object in respect to a first coordinate system may be transformed to another form in respect to a second coordinate system.

The registration data may be configured to define transformation relationships of various types of coordinate systems. For example, the registration data may define the transformation relationships between a coordinate system of a virtual spatial sensor marker and a coordinate system of a virtual instrument. In this example, spatial properties in respect to the virtual instrument may be transformed into spatial properties in respect to the virtual spatial sensor marker.

For another example, the registration data may define the transformation relationships between a coordinate system of a virtual anatomy and a coordinate system of a virtual environment. In this example, spatial properties in respect to the virtual anatomy may be transformed into spatial properties in respect to the virtual environment. By adopting the coordinate transformation, the virtual anatomy shares a same coordinate system with the virtual environment, therefore allowing the virtual anatomy is to be positioned into the virtual environment.

In Step S3190, the processor 1710 receives a least one set of medical operation plan data from a medical operation plan data source 3193. The medical operation plan data source 3193 may be the storage unit of the robotic system 1000, other external memory device or other external processing device. The medical operation plan data is configured for representing predetermined medical operation performed by the robotic system 1000. Medical operation plan data may include virtual objects for representing anatomical site and virtual objects for representing predetermined medical operation. The virtual objects of the medical operation plan data may include identity, spatial properties (e.g., position or orientation), shape, size or other object properties. Specifically, the identity of virtual objects of the medical operation plan data may be a planning object, an instrument, an anatomical site, or other objects.

The planning object is a geometric concept that represents a predetermined interaction with an instrument 1200 or an anatomical site 3701. The planning object may include a planning object boundary (POB) and a planning object attribute (POA). The POB is the geometric boundary of a planning object. The POA is configured to define the characteristic of interaction between the planning object and the instrument.

The medical operation plan may be generated by a planning module of the computer system of the robotic system 1000. A user of the robotic system 1000 may assign the POB and the POA of a planning object to generate a medical operation plan, and output the medical operation plan as a set of medical operation plan data.

In the present disclosure, the term "virtual planning object" refers to a virtual object for representing a planning object. A virtual planning object may comprises a variety of object properties, such as identity, spatial properties (e.g., position, and orientation), three-dimensional graphic properties (e.g., shape, and size), and virtual planning object attribute (VPOA).

The identity of a virtual planning object may be a planning object defined by the user of the robotic system 1000, or by the robotic system 1000 itself, or both. For example, the identity of a virtual planning object may be a human defined drilling trajectory of a spine surgery. For another example, the identity of a virtual planning object may be a computer generated sampling route in a registration process for generating registration data.

The spatial properties (e.g., position and/or orientation) of the virtual planning object may be defined by the user of the robotic system 1000. Usually, the position/orientation of the virtual planning object has a fix spatial relationship with a virtual anatomy. For example, between a virtual planning of trajectory and virtual anatomy, there may exist a transformation matrix to represent their spatial relationships.

The shape of a virtual planning object may include a virtual planning object boundary (VPOB). The VPOB is configured to define the range of space of a virtual planning object. A VPOB may be a boundary in a variety geometric space systems. For example, a VPOB may be points in an one-dimensional space, a closed loop in a two-dimensional space, or a closed surface in a three-dimensional space. A POB may form a variety shapes. For example, a VPOB may form a spherical closed surface, or an arbitrary shaped surface.

A VPOA is configured to define a characteristic of a region enveloped by at least one VPOB. The characteristic may be chosen from a list of POA. The list of POA include interactions between an instrument 1200 and an anatomical site, such as drilling, milling, cutting, sampling for registration. For example, a POA may define a curve linear region within a POB as a drilling trajectory. The list of POA may further includes a characteristic for indicating that an instrument should not be present in the region or indicating a restricted region that should not be effected by the tool 1250. In such example, a VPOA may define a volume within a virtual VPOB as the restricted region for the tool 1250. Furthermore, the list of POA may also include a set of vectors for representing the set of valid orientation of the tool 1250.

The list of planning object attribute may further include a characteristic for indicating that a function of the robotic system 1000 should be switched on or off. For examples, a planning object attribute (POA) may define a volume enveloped by a planning object boundary (POB) as an auto-pilot region. An auto-pilot region is a region in which the manipulator 1210 may automatically control the position and orientation of a tool 1250.

Figure 12:
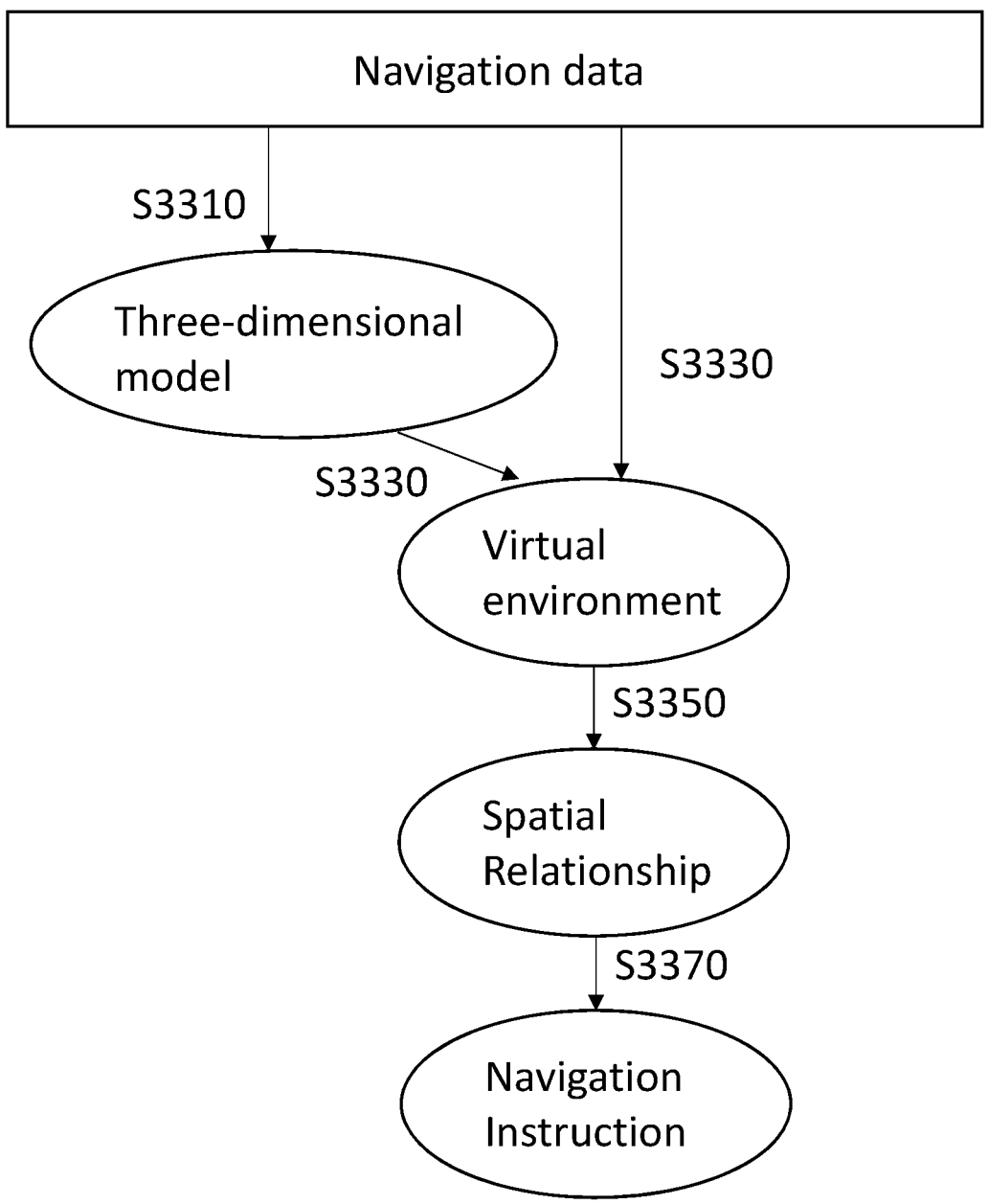
FIG. 12 is a block diagram showing the steps of generating virtual environment and navigation instruction in the navigation method in accordance with an embodiment of the present disclosure.

Referring to FIG. 12. According to an embodiment, the step of generating the virtual environment and the navigation instruction (S3300) may include the steps of: (S3310) preparing a three-dimensional model; (S3330) generating the virtual environment; (S3350) determining spatial relationship of a virtual workspace or of a virtual active space; and (S3370) generating the navigation instruction. It is to be understood that the steps of S3110, S3130, S3150, S3170, S3190 are presented herein without particular order; in other words, the steps may be performed separately, simultaneously, or sequentially in a specific order.

In Step S3310, at least one virtual object with its shape is obtained. For example, the robotic system 1000 may execute a three-dimensional computer graphics process to define the shape of the a least one virtual object. For another example, the robotic system 1000 may load a virtual object having a well-defined shape from a user's input or from the navigation data.

More specifically, in an embodiment, the robotic system 1000 executes a three-dimensional computer graphics process to define the shape of a virtual anatomy. In this embodiment, the three-dimensional computer graphics process may include tomographic reconstruction and segmentation. In tomographic reconstruction, the robotic system 1000 utilizes a set of anatomical images to generate a three-dimensional model. The set of anatomical images may be a set of CT slices. On the other hand, in segmentation, the robotic system 1000 may separate a three-dimensional model of an anatomy into at least two partitions according to their corresponding physiological information. For example, a virtual anatomy representing a spine may be separated into multiple virtual vertebras.

In another embodiment, the robotic system 1000 may execute a three-dimensional computer graphics process to define a partial shape of a virtual anatomy. For example, three-dimensional meshes may only depict a set of specific boundary of the virtual object. The set of the specific boundary may include outer surface of a virtual anatomy or arbitrary boundary assigned by the user of the robotic system. For another example, three-dimensional meshed may only depict an simple model to represent spatial properties of a virtual object, by using, for example, an arrow icon to represent orientation of a virtual object.

Figure 13:
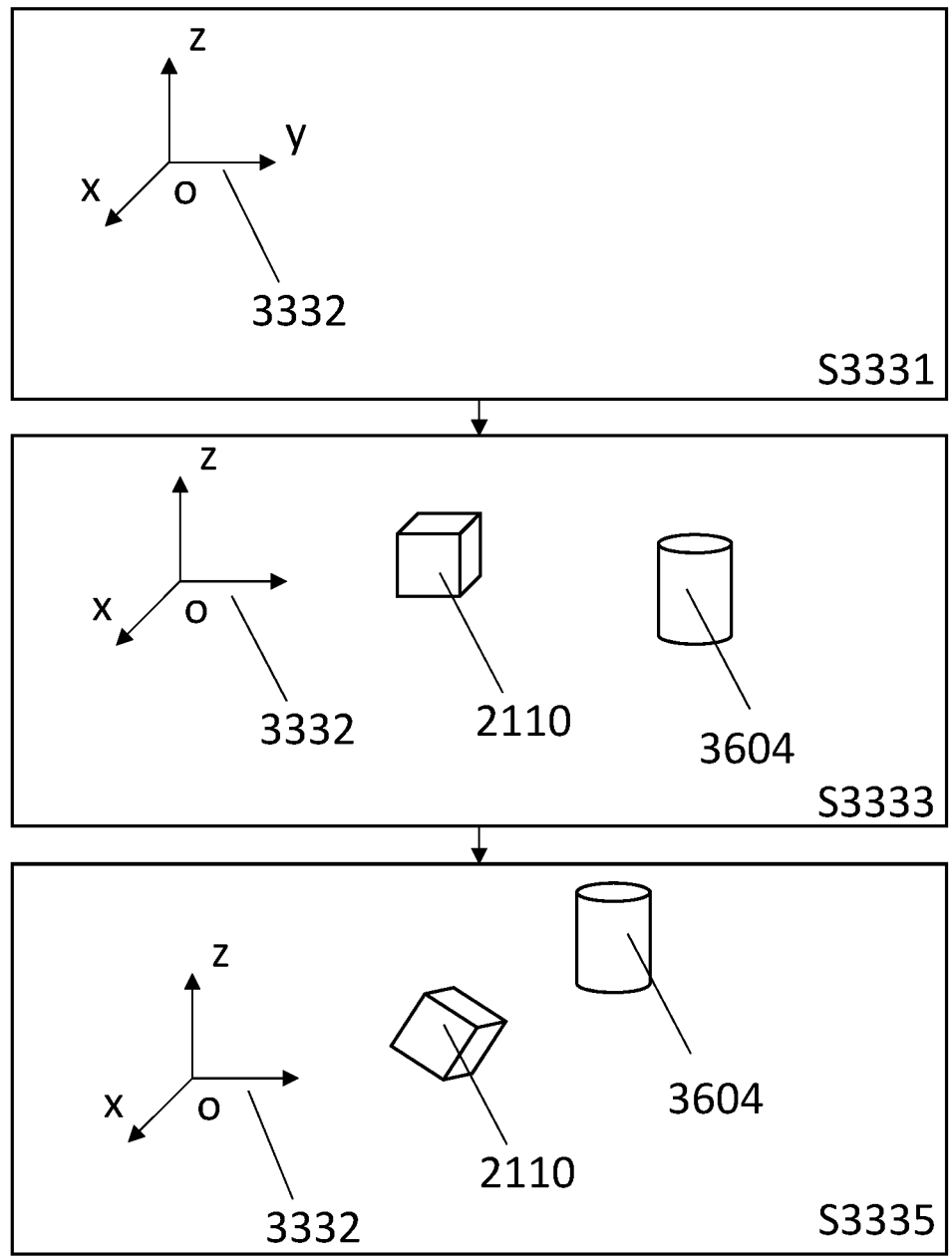
FIG. 13 is a block diagram showing the steps of generating virtual environment in accordance with an embodiment of the present disclosure.

Referring to FIG. 13. According to an embodiment, the robotic system 1000 generates in Step (S3330) a virtual environment to represent a medical operation environment.

The Step S3330 may include the steps of: (S3331) defining the well-defined coordinate system, (S3333) registering the virtual objects, and (S3335) updating spatial properties of the virtual objects. It is to be understood that the steps of S3110, S3130, S3150, S3170, S3190 are presented herein without particular order; in other words, the steps may be performed separately, simultaneously, or sequentially in a specific order.

In Step S3331, the robotic system 1000 may generate a virtual space by defining the well-defined coordinate system 3332. In the virtual space, an origin point and the unit of the axes/coordinates are well-defined. For example, the coordinate system of the virtual space may be defined by an observation coordinate system of the spatial sensor system 1500. For example, the origin point of the coordinate system of the virtual space may be defined by a position of a spatial sensor marker located on an anatomical site.

In Step S3333, the robotic system 1000 may define spatial relationship between the virtual object and the virtual space. In other words, the spatial properties of at least one virtual object in respect to the coordinate system of the virtual space are well-defined by the robotic system 1000. For example, the robotic system 1000 may define the position of a virtual anatomy 2110 and a virtual instrument 3604 respect to the virtual space based on a set of the registration data. For another example, the robotic system 1000 may define the position and orientation of the endoscope image data through the corresponding registration data. The registration of the endoscope image data to the virtual environment allowed the image/video of the endoscope image data to be displayed on the virtual anatomy, so that the endoscope image data spatially and timely coincides with the virtual anatomy in the virtual environment.

In Step S3335, the robotic system 1000 may automatically modify the spatial properties of every virtual object in the virtual space by updating the spatial sensor data. For example, the position/orientation of the virtual anatomy 2110 and the virtual instrument 3604 may change during a medical operation, therefore the robotic system 1000 may continuously receive the spatial sensor data and update the position/orientation. As a result, the virtual objects in the virtual space may dynamically mimic the real medical operation environment.

Referring again to FIG. 12, in Step S3350, the robotic system 1000 determines a spatial relationship of the virtual object according to the virtual environment 3600 generated in Step S3330. The spatial relationship is determined based on calculation of object properties of the virtual objects of interest. For example, in order to determine spatial relationship between a virtual active space and a virtual planning object, object properties such as the spatial properties (e.g., position or orientation), the shapes, and the VPOB, may be calculated. In this example, the robotic system 1000 may determine whether the virtual planning object overlaps with the virtual active space. Additionally, since the virtual environment 3600 is a dynamic system, the spatial relationship determined in Step S3350 is also dynamically updated according to the dynamically altered object properties of the virtual objects in the virtual environment 3600.

In some embodiments, the spatial relationship may be determined numerically. For example, the robotic system 1000 may obtain a compensation rating of the instrument 1200. The compensation rating is a function of a plurality of independent variables, which include spatial properties (e.g., position and orientation) of the virtual instrument corresponding to the instrument 1200, shape (or geometric boundary) of the virtual workspace or virtual active space of the instrument 1200, spatial properties of at least one virtual planning object, and shapes of the at least one virtual planning object. The value of a compensation rating represents the capability of the manipulator 1210 of the instrument 1200 in manipulating spatial properties of the tool 1250 to correct spatial deviation of the instrument from a predetermined medical operation plan, according to the current spatial properties of the instrument 1200.

For example, the value of the compensation rating may be set to minimum, such as zero in a zero-to-ten scale, when the position, orientation or both the position and orientation of the virtual instrument 3604 is not in a range, in which the virtual workspace of the virtual instrument 3604 does not cover a virtual planning object, therefore prohibiting the instrument 1200 from effectively using the manipulator 1210 to manipulate the tool 1500 according to a predetermined medical operation plan. For another example, the value of the compensation rating may be set to maximum, such as ten in a zero-to-ten scale, when the position, orientation or both the position and orientation of an virtual instrument 3604 is in a range, in which the virtual workspace of the virtual instrument 3604 covers a virtual planning object, therefore allowing the instrument 1200 to effectively use the manipulator 1210 to manipulate the tool 1500 according to a medical operation plan.

Referring again to FIG. 12. The robotic system 1000 generates in Step S3370 the navigation instruction 3602 and/or output the navigation instruction 3602. The navigation instruction 3602 may be received by the user interface 1800 to be presented to the user of the robotic system 1000.

In Step S3370, the robotic system 1000 generates at least one navigation instruction 3602 and output the navigation instruction 3602 for presenting to the user of the robotic system 1000. The navigation instruction 3602 is computer generated suggestion of manual manipulation of the instrument 1200 according to the spatial relationship determined in Step S3350. For example, in Step S3370, the robotic system 1000 may generate a navigation instruction 3602 to suggest the user of the robotic system 1000 to move the instrument 1200 manually to a specific position or to maintain the orientation of the instrument 1200 within a specific range of orientation.

In the embodiments, the user of the robotic system 1000 may be informed by observing the spatial relationship and then taking corresponding actions of manipulation. For example, during a medical operation, the user may receive an navigation instruction, which points out that the workspace of the instrument is not included a target anatomical site; therefore, the user may manually adjust the position/orientation of the instrument 1200 accordingly. For another example, during the medical operation, the user may receive a compensation rating on the current position/orientation of the instrument 1200, therefore comprehend the ability of compensation of the instrument 1200 in respect to the current position/orientation of the instrument 1200 according to the medical operation plan; thereafter, the user may manually adjust the position/orientation of the instrument 1200 accordingly.

In some embodiments, the robotic system 1000 generates the navigation instruction 3602 according to a positional relationship or orientational relationship between the virtual objects in the virtual environment. For example, the navigation instruction may inform the user of the robotic system 1000 to change the position/orientation of the instrument. For another example, the robotic system 1000 may generate the navigation instruction 3602 according to a positional relationship between the virtual instrument and the virtual planning object and according to the virtual planning object attribute (VPOA) of the virtual planning object.

In some embodiments, the robotic system 1000 may generate a navigation instruction 3602 that is configured to inform the user(s) of the robotic system 1000 that the robotic system 1000 is in a safe state. The safe state may be the state in which the robotic system 1000 is in compliance with a predetermined medical operation plan. For example, the safe state may be the condition in which the instrument is not at an undesired position.

In some embodiments, the robotic system 1000 may generate a navigation instruction 3602 that is configured to inform the user(s) of the robotic system 1000 that the robotic system 1000 is in an unsafe state. The unsafe state may be the state in which the robotic system 1000 is not in compliance with the predetermined medical operation plan. For example, the safe state may be the condition in which the instrument is at an undesired position.

In Step S3370, the navigation instruction 3602 generated by the robotic system 1000 may be outputted as data of text, script, two-dimensional or three-dimensional images.

In some embodiments, Step S3300 may further include a step of: (S3390) generating control signal (not shown in figures). In Step S3390, the robotic system 1000 may generate at least one set of control signal according to the at least one spatial relationship determined in Step S3350. For example, according to the spatial relationship determined in Step S3350, the robotic system 1000 may generate a control signal for activating or inactivating at least one function of the instrument 1200.

In the Step S3500, the virtual environment and/or the navigation instruction are presented to the user(s) of the robotic system 1000 via the user interface 1800. The presentation of the virtual environment and the navigation instruction may be performed visually, audibly, and/or by other means.

Figure 14:
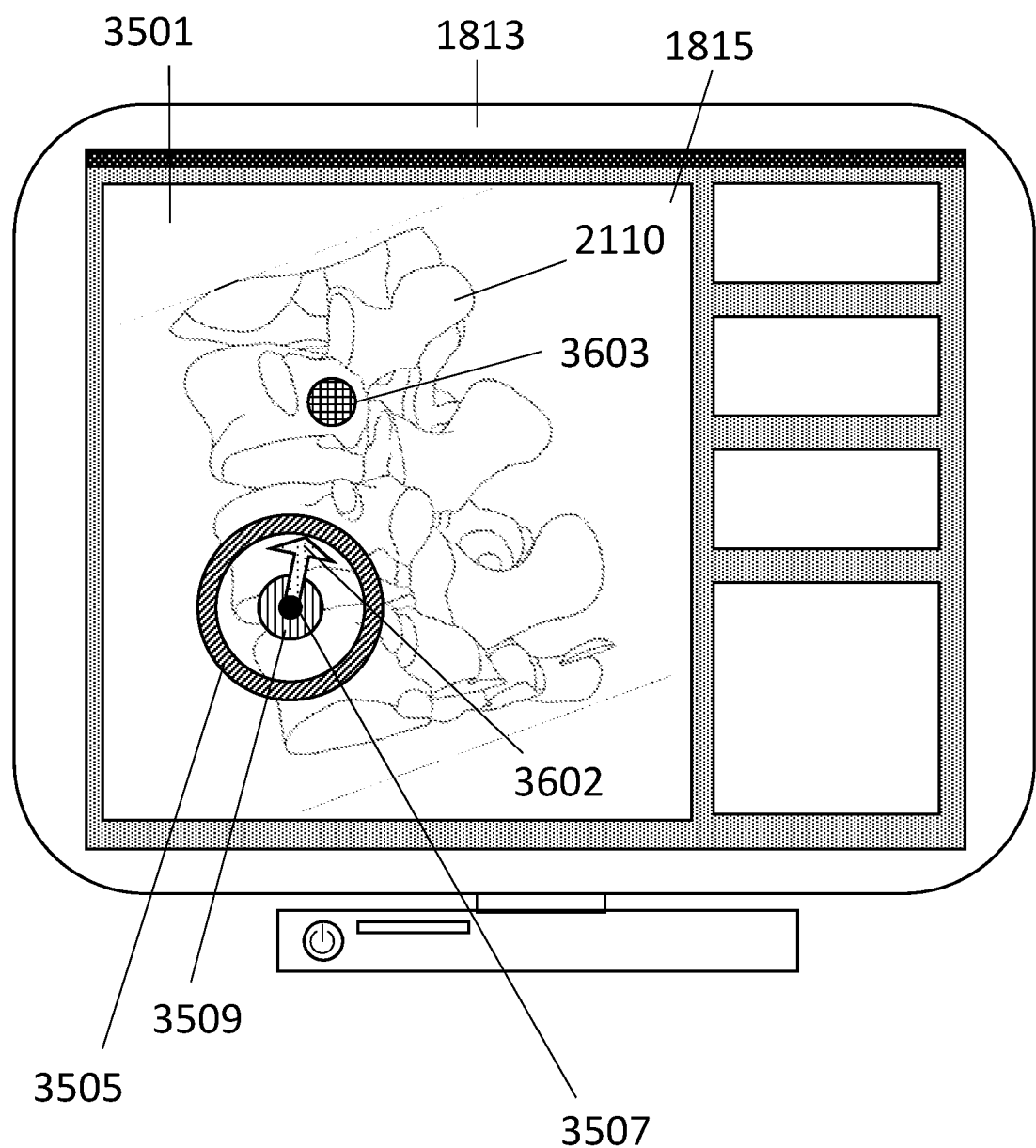
FIG. 14 is a schematic illustration of the step of presenting virtual environment and navigation instruction in the navigation method in accordance with an embodiment of the present disclosure.

Referring to FIG. 14. According to an embodiment of the present disclosure, Step S3500 includes a step of: (S3510) rendering the virtual environment 3600 and/or the navigation instruction 3602. In this embodiment, the virtual environment 3600 and the navigation instruction 3602 are presented visually, by rendering and displaying the three-dimensional graphics of the virtual environment 3600 and/or the navigation instruction 3602. Renders 3501 generated in Step S3510 may be displayed on a display device 1813.

In Step S3510, the processor 1710 may generate images of a virtual environment from a specific point of view. For example, usually, a virtual camera at a specific position is configured to capture the virtual environment. The images or videos of the virtual environment captured by the virtual camera is then displayed on a display device. The images generated by the rendering process may be called renders 3501.

The rendering process should be known by those of ordinary skill in the art as three-dimensional computer graphics. Rendering are often described by a computer graphics pipeline. Application Programming Interfaces (API) were created to unify steps of the graphic pipeline for various type of three-dimensional graphics hardware. For example, the API may be a Visualization Toolkit (VTK) system, a Direct3D system, or an OpenGL system. To display the layout on the display device 1813, a graphic pipeline may be executed. The display device 1813 may be television sets, computer monitors, panels, or head-mounted displays.

In some embodiments, the renders generated by the rendering process may be integrated with a graphical user interface (GUI) application 3503. The GUI application 3503 of the robotic system 1000 may include regions for displaying the three-dimensional renders. Other regions may provide other functions, such as function for displaying pre-operative anatomical images, function for manipulator control or other functions.

In some embodiments, in addition to the rendering, the GUI application of the robotic system 1000 may be capable of utilizing the navigation data, virtual environment 3600, and navigation instruction 3601 of the navigation method 3000 to generate graphics.

Referring to FIG. 14, an exemplary embodiment of the GUI application 1815 displayed on the display device 1813 is depicted. The GUI application 1815 includes of the renders 3501 of the virtual environment. The renders 3501 includes the virtual anatomy 2110 and the virtual planning object 3603. In this embodiment, the rendering is taken from a viewing angle that is parallel to the direction of the orientation of the instrument 1200.

In the embodiment, the GUI application 1815 also displays a set of two-dimensional icons generated by the GUI application 1815. The set of two-dimensional icons overlap and interact with the renders 3501. The set of two-dimensional icons may include a donut icon 3505, a circular point icon 3507, and a circle icon 3509. The position of the donut icon 3505 represents the position of the active space according to the instrument in real space. The position of the circular point icon 3507 represents the position of the tip of the tool 1250 of the instrument 1200.

In the embodiment, the GUI application 1815 may also display the navigation instruction 3602 to provide a suggested direction of movement of the instrument 1200. The navigation instruction 3602 may be a three-dimensional model renders or a GUI generated two-dimensional icon.

Figure 15:
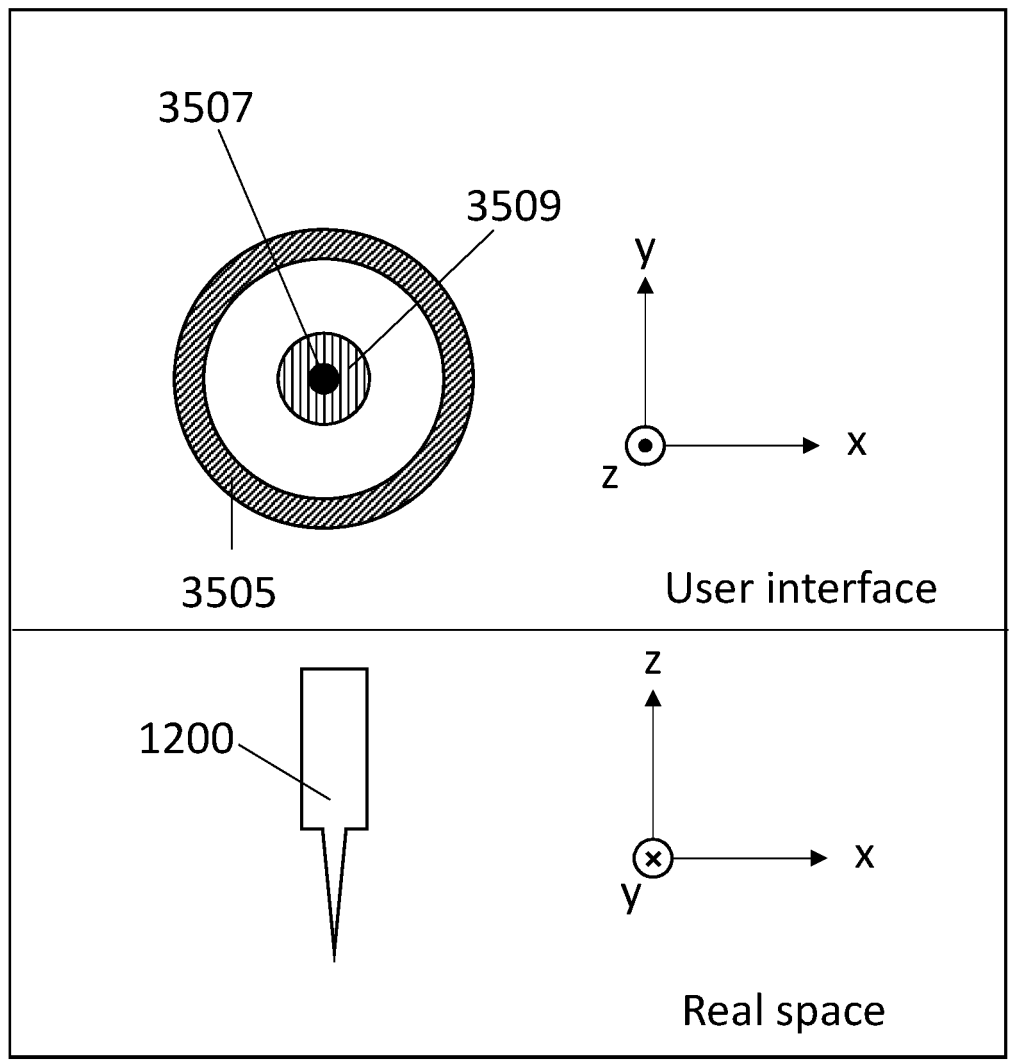
FIG. 15 is a schematic illustration of a user interface of the robotic system accordance with an embodiment of the present disclosure.
Figure 16:
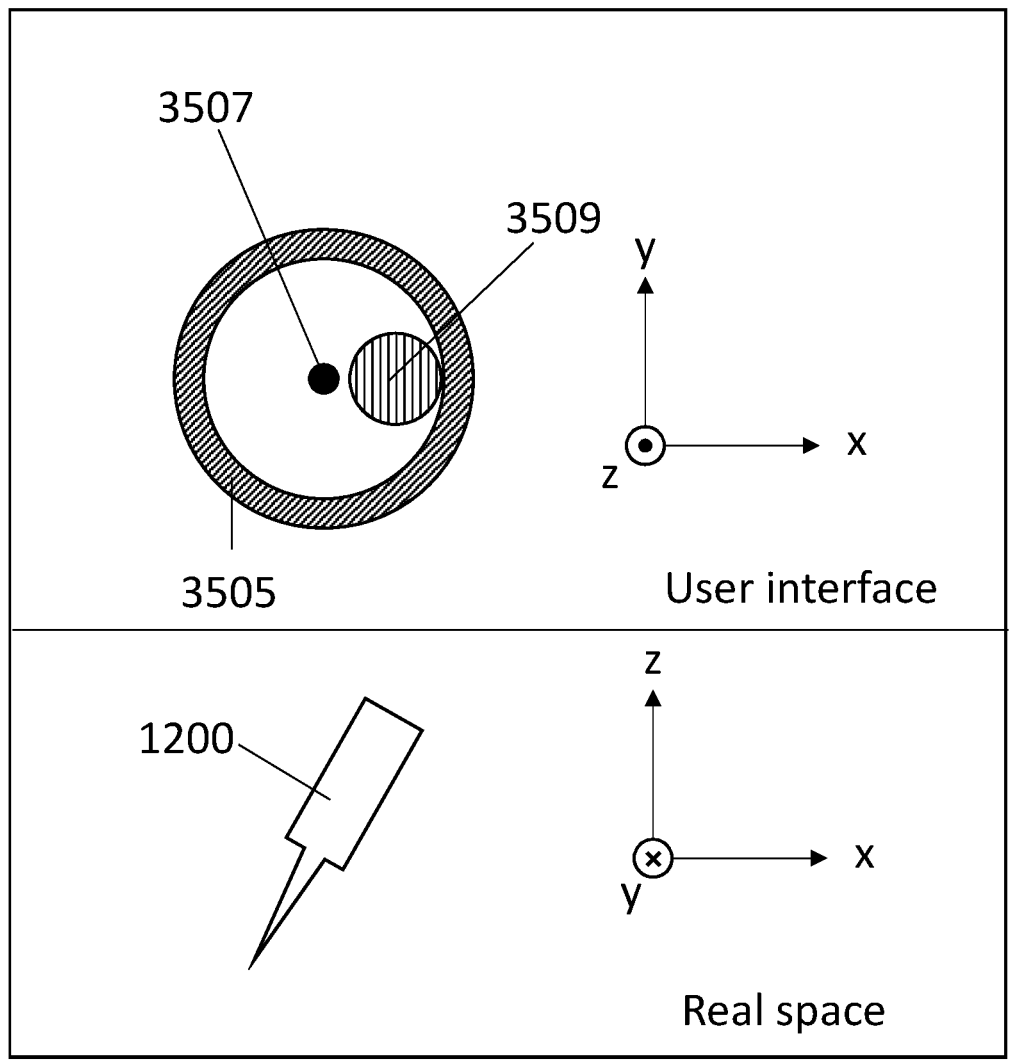
FIG. 16 is a schematic illustration of two dimensional icons generated by a graphic user interface (GUI) application of the robotic system in accordance with an embodiment of the present disclosure.
Figure 17:
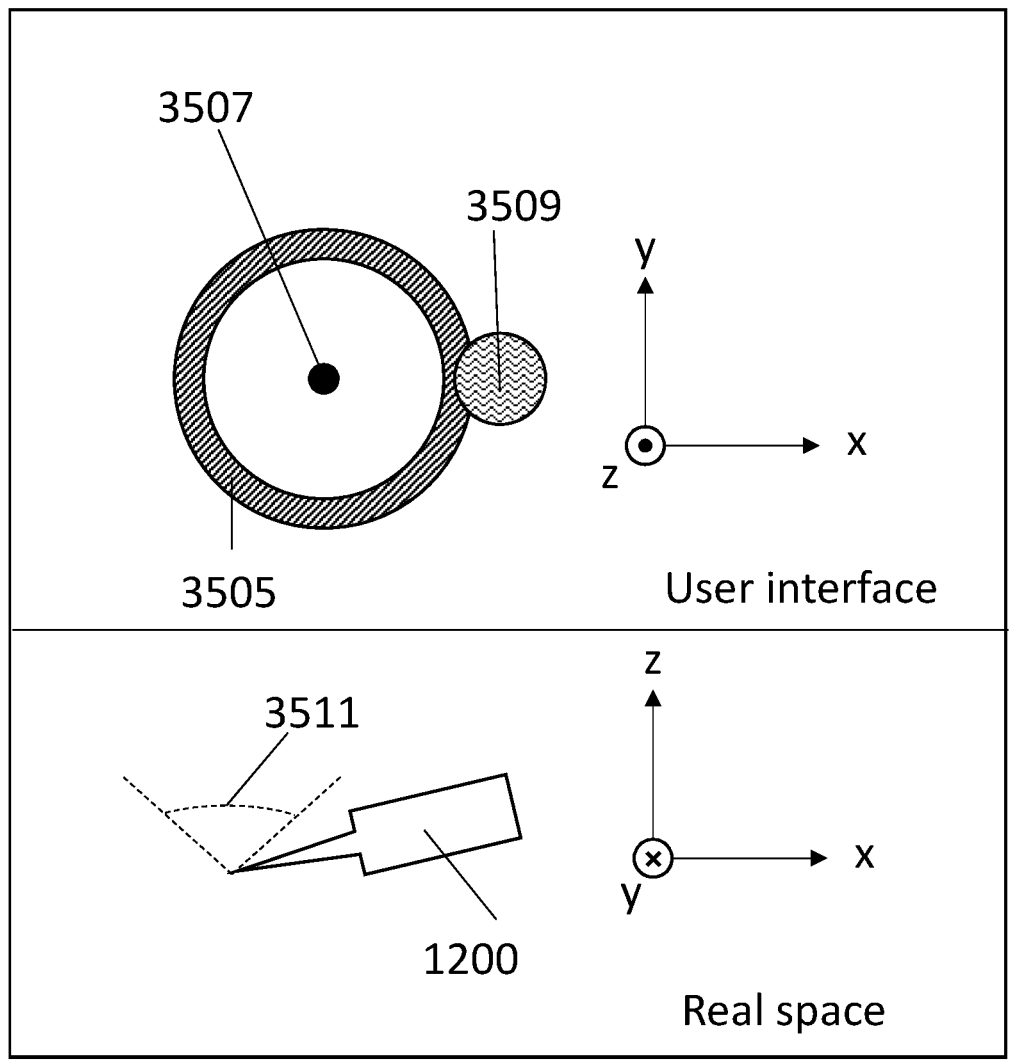
FIG. 17 is another schematic illustration of two dimensional icons generated by the GUI application in accordance with an embodiment of the present disclosure.

In the embodiment, the circle icon 3509 is movable in respect to the donut icon 3505. The relative position of the circle icon 3509 respecting to the donut icon 3505 represents the orientation of the instrument 1200. As exemplified in FIG. 15, FIG. 16, and FIG. 17, the orientation of the instrument 1200 may be obtained from the spatial sensor data of the instrument 1200 and then be presented by the relative position of the circle icon 3509 in respect to the donut icon 3505. In FIG. 15, the instrument 1200 is oriented parallel to the z axis, and the circle icon 3509 is thereby positioned at the center of the donut icon 3505. In FIG. 16, the instrument 1200 is oriented at an angle on the x axis in respect to the z axis, and the circle icon 3509 is thereby positioned as displacement from the center of the donut icon 3505 along the x direction. In FIG. 17, the instrument 1200 is oriented at an angle on the x axis in respect to the z axis, and the angle exceeds a predetermined range of valid orientation 3511 of the instrument 1200. In some embodiments, the predetermined range of valid orientation 3511 of the instrument 1200 may be described in a VPOA of a virtual planning object or in the instrument data to represent a predetermined range of angle of a medical operation, for example, the medical operation may be drilling the spine. In some other embodiments, the predetermined range of valid orientation 3511 of the instrument 1200 may be defined as a range whether the virtual workspace or virtual active space is completely covering a virtual planning object according to the orientation of the virtual instrument 3604 disregarding to the relative position of the virtual instrument 3604 and the considering virtual planning object. The color of the circle icon 3509 may change to inform the user that the orientation of the instrument 1200 exceeds the range of valid orientation 3511.

In some other embodiments, the virtual environment or the two-dimensional icons may represent an workspace progress bar of a medical operation. For example, the workspace progress bar may be generated according to the ratio of a distance between an endpoint of a predetermined drilling plan route and a point of a workspace/active space of the instrument. By referencing to the workspace progress bar, the user is provided a sense of whether a predetermined medical operation can be completed at the current position/orientation of the instrument, or whether the user has to move or manipulate manually the instrument to an optimal position or orientation to complete the predetermined medical operation.

In the embodiments, the workspace progress bar may be displayed as a color bar on the donut icon 3505 in a circumference direction. For another example, the workspace progress bar may be displayed as a three-dimensional model rendering.

According to an embodiment of the present disclosure, the step of presenting the virtual environment and the navigation instruction (S3500) may further include a step of: displaying the endoscope image data. The endoscope image data may be displayed on a virtual endoscope display plane registered in the virtual environment. Alternatively, the endoscope image data may be displayed on a GUI generated region superimposed on the rendering of the virtual environment. Since the endoscope image data is acquired by the endoscope device 4110 at a specific camera angle, the user interface may provide a control panel to allow the user of the robotic system to manipulate the viewing angle of rendering of the virtual environment. If the viewing angle of rendering coincides with the camera angle, the user is allowed to observe the endoscope image data augmented on the virtual environment; in other words, the endoscope image data spatially and timely coincides with the virtual anatomy in the virtual environment.

In the navigation method 3000 according to an embodiment of the present disclosure, the step of presenting the virtual environment and the navigation instruction (S3500) may further include a step of: (S3520) presenting the virtual environment and navigation instruction in another type of presentation.

In an embodiment, the robotic system 1000 may use the manipulator to indicate a direction towards a specific destination so that the user of the robotic system 1000 may reference to the indicated direction to move the instrument 1200. In another embodiment, the robotic system 1000 may include a light indicator. The light indicator may include at least one subgroup lighting elements for representing a specific direction, so that the user of the robotic system 1000 may reference to the direction to move the instrument. For example, the light indicator may be a device including an array of light emitting diodes. In yet another embodiment, the robotic system 1000 may use an audio module to inform the user the navigation instruction by audio signals. For example, the robotic system 1000 may provide an alert sound to describe the navigation instruction.

In sum, according to the various embodiments of the present disclosure, the robotic system 1000 utilizes data regarding the workspace of the manipulator 1210 of the instrument 1200 to provide navigation instructions 3602 to a user of the robotic system 1000. By referencing to the navigation instructions 3602, the user of the robotic system 1000 is provided a sense of the capability of the instrument to correct deviations of the position or orientation of the tool 1250 from a predetermined medical operation plan, according to the position and/or orientation of the instrument 1200.

Further, the navigation instructions also inform the user of the suggestions on how to manually manipulate the instrument to an optimal position or orientation to improve the capability of the instrument to correct the deviations of the position or orientation of the tool 1250 from the predetermined medical operation plan, according to the position and/or orientation of the instrument 1200.

Previous descriptions are only embodiments of the present disclosure and are not intended to limit the scope of the present disclosure. Many variations and modifications according to the claims and specification of the disclosure are still within the scope of the claimed disclosure. In addition, each of the embodiments and claims does not have to achieve all the advantages or characteristics disclosed. Moreover, the abstract and the title only serve to facilitate searching patent documents and are not intended in any way to limit the scope of the claimed disclosure.

What is claimed is:

1. A navigation method for a medical operation and implemented by a robotic system using a tool, the method comprising:
   receiving, at a processor of the robotic system, at least one set of navigation data, wherein:
      the at least one set of navigation data includes at least one set of registration data, at least one set of instrument data, at least one set of spatial sensor data, and at least one set of medical operation plan data,
      the at least one set of spatial sensor data includes information generated from signals transmitted from a spatial marker frame,
      the robotic system includes an instrument of an instrument system and a support arm coupled to the instrument, the instrument having a housing providing a handle and a manipulator mechanically attached to the housing, the manipulator having a platform coupled to the tool, a base, joints coupling the base and the platform, and actuators aligned parallel to each other, located inside the housing, and configured to drive movement of the joints, and the spatial marker frame disposed on the platform,
      the handle is disposed between the manipulator and the support arm,
      the at least one set of instrument data comprises at least one set of a virtual workspace of the robotic system or a virtual active space of the robotic system, and
      the at least one set of navigation data comprises at least one virtual object used to generate a representation of an anatomical site and a representation of the instrument system;
   receiving or generating, at the processor of the robotic system, at least one three-dimensional model of the at least one virtual object;
   processing, at the processor of the robotic system, the at least one set of navigation data to generate a virtual environment, the virtual environment including the at least one set of the virtual workspace or the virtual active space and the at least one virtual object;
   processing, at the processor of the robotic system, the at least one set of navigation data and the virtual environment to determine at least one spatial relationship between the at least one set of the virtual workspace or the virtual active space and the at least one virtual object for generating at least one navigation instruction, wherein the at least one set of the virtual workspace or the virtual active space is determined based on a workspace of the manipulator, the workspace of the manipulator including a set of reachable points of the tool when the base is maintained static; and
   presenting, at a user interface electrically connected to the robotic system, at least one of the virtual environment and the at least one navigation instruction of the robotic system for reference during the medical operation.

2. The navigation method according to claim 1, wherein receiving, at the processor of the robotic system, the at least one set of navigation data comprises receiving at least one set of anatomical data.

3. The navigation method according to claim 2, wherein:
   receiving the at least one set of anatomical data comprises receiving at least one set of endoscope image data from a minimally invasive image system electrically connected to the robotic system, and
   presenting, at the user interface electrically connected to the robotic system, the at least one of the virtual environment and the at least one navigation instruction of the robotic system comprises displaying the at least one set of endoscope image data, wherein the at least one set of endoscope image data spatially and timely coincides with a virtual anatomy in the virtual environment.

4. The navigation method according to claim 1, wherein the virtual active space comprises a first virtual active space and a second virtual active space, and a size or a shape of the first virtual active space is different from a size or a shape of the second virtual active space.

5. The navigation method according to claim 4, wherein:
   the robotic system is electrically connected to the instrument system,
   the first virtual active space is associated with one of a plurality of criteria for activating the manipulator or the tool, and
   the second virtual active space is associated with one of a plurality of criteria for inactivating the manipulator or the tool.

6. The navigation method according to claim 1, wherein:
   the at least one spatial relationship comprises at least one compensation rating, and
   the at least one compensation rating is calculated from the at least one set of medical operation plan data and the virtual workspace or from the at least one set of medical operation plan data and the virtual active space.

7. The navigation method according to claim 1, wherein:
   processing, at the processor of the robotic system, the at least one set of navigation data and the virtual environment comprises processing at least one virtual planning object attribute in the at least one set of medical operation plan data to generate the at least one navigation instruction, and
   the at least one virtual planning object attribute represents a trajectory of the tool during the medical operation.

8. The navigation method according to claim 1, further comprising generating at least one set of control signals for controlling at least one function of the robotic system.

9. The navigation method according to claim 8, wherein:
   the at least one set of control signals comprises a first control signal and a second control signal,
   the first control signal is generated according to a first calculation result of a calculation of the at least one set of navigation data, and
   the second control signal is generated according to a second calculation result of the calculation of the at least one set of navigation data.

10. The navigation method according to claim 1, wherein:
presenting, at the user interface electrically connected to the robotic system, the at least one of the virtual environment and the at least one navigation instruction comprises rendering three-dimensional graphics on a display device electrically connected to the processor, and
the three-dimensional graphics comprise at least one of the virtual environment, the at least one navigation instruction, the virtual environment and the at least one navigation instruction.

11. The navigation method according to claim 10, wherein a viewing angle of the rendering is aligned with an orientation of an instrument electrically connected to the robotic system.

12. The navigation method according to claim 1, wherein:
presenting, at the user interface electrically connected to the robotic system, comprises generating and displaying, by a graphical user interface (GUI) application, a plurality of two-dimensional icons according to the at least one set of navigation data and the virtual environment, and
the two-dimensional icons represent a position of an instrument electrically connected to the robotic system, an orientation of the instrument, the at least one navigation instruction, and a range of valid orientation of the instrument.

13. The navigation method according to claim 1, wherein:
the at least one navigation instruction is presented by a light indicator or an audio device, and
the light indicator and the audio device are electrically connected to the robotic system.

14. The navigation method according to claim 1, wherein the at least one navigation instruction is presented by a direction of the tool.

15. The navigation method according to claim 1, wherein presenting, at the user interface electrically connected to the robotic system, comprises generating and displaying, by a graphical user interface (GUI) application, a plurality of two-dimensional icons according to the at least one set of navigation data and the virtual environment, wherein the two-dimensional icons represent a workspace progress bar.

16. The navigation method according to claim 1, wherein each of the actuators is coupled to the base.

17. The navigation method according to claim 16, wherein each of the joints is coupled to one of the base and the platform.

18. A robotic system using a tool for assisting a medical operation, the robotic system comprising:
an instrument system having an instrument and a support arm coupled to the instrument, the instrument having a housing providing a handle and a manipulator mechanically attached to the housing, the manipulator having a platform coupled to the tool, a base, joints coupling the base to the platform, and actuators aligned parallel to each other, located inside the housing, and configured to drive movement of the joints, wherein the handle is disposed between the manipulator and the support arm and a spatial marker frame is disposed on the platform;
a user interface electrically connected to the robotic system; and
a computer system electrically connected to the user interface and the instrument system, wherein the computer system comprises at least one processor and at least one non-transitory computer readable medium coupled to the at least one processor and storing computer-readable instructions for navigating the medical operation that, when executed by the at least one processor, cause the robotic system to:
receive at least one set of navigation data, wherein:
the at least one set of navigation data includes at least one set of registration data, at least one set of instrument data, at least one set of spatial sensor data, and at least one set of medical operation plan data,
the at least one set of spatial sensor data includes information generated from signals transmitted from the spatial marker frame,
the at least one set of instrument data is used to generate at least one set of a virtual workspace of the robotic system or a virtual active space of the robotic system,
the at least one set of navigation data is used to generate at least one virtual object, and
the at least one virtual object includes a representation of an anatomical site and a representation of the instrument system;
receive or generate at least one three-dimensional model of the at least one virtual object;
process the at least one set of navigation data to generate a virtual environment, the virtual environment including the at least one set of the virtual workspace or the virtual active space and the at least one virtual object;
process the at least one set of navigation data and the virtual environment to determine at least one spatial relationship between the at least one set of the virtual workspace or the virtual active space and the at least one virtual object for generating at least one navigation instruction, wherein the at least one set of the virtual workspace or the virtual active space is determined based on a workspace of the manipulator, the workspace of the manipulator including a set of reachable points of the tool when the base is maintained static; and
present, at the user interface electrically connected to the robotic system, at least one of the virtual environment and the at least one navigation instruction of the robotic system for reference during the medical operation.

19. The robotic system according to claim 18, wherein receiving the at least one set of navigation data comprises receiving at least one set of anatomical data.

20. The robotic system according to claim 19, wherein:
receiving the at least one set of anatomical data comprises receiving at least one set of endoscope image data from a minimally invasive image system electrically connected to the robotic system, and
presenting, at the user interface electrically connected to the robotic system, the at least one of the virtual environment and the at least one navigation instruction comprises displaying the at least one set of endoscope image data, wherein the at least one set of endoscope image data spatially and timely coincides with a virtual anatomy in the virtual environment.

21. The robotic system according to claim 18, wherein:
the virtual active space comprises a first virtual active space and a second virtual active space, and a size or a shape of the first virtual active space is different from a size or a shape of the second virtual active space.

22. The robotic system according to claim 21, wherein:
the robotic system is electrically connected to the instrument system,
the first virtual active space is associated with one of a plurality of criteria for activating the manipulator or the tool, and the second virtual active space is associated with one of a plurality of criteria for inactivating the manipulator or the tool.

23. The robotic system according to claim 18, wherein:
the at least one spatial relationship comprises at least one compensation rating, and
the at least one compensation rating is calculated from the at least one set of medical operation plan data and the virtual workspace or from the at least one set of medical operation plan data and the virtual active space.

24. The robotic system according to claim 18, wherein:
processing the at least one set of navigation data and the virtual environment comprises processing at least one virtual planning object attribute in the at least one set of medical operation plan data to generate the at least one navigation instruction, and
the at least one virtual planning object attribute represents a trajectory of the tool during the medical operation.

25. The robotic system according to claim 18, wherein the computer-readable instructions, when executed by the at least one processor, further cause the robotic system to generate at least one set of control signals for controlling at least one function of the robotic system.

26. The robotic system according to claim 25, wherein:
the at least one set of control signals comprises a first control signal and a second control signal,
the first control signal is generated according to a first calculation result of a calculation of the at least one set of navigation data, and
the second control signal is generated according to a second calculation result of the calculation of the at least one set of navigation data.

27. The robotic system according to claim 18, wherein:
presenting, at the user interface electrically connected to the robotic system, the at least one of the virtual environment and the at least one navigation instruction comprises rendering three-dimensional graphics on a display device electrically connected to the at least one processor, and
the three-dimensional graphics comprise at least one of the virtual environment, the at least one navigation instruction, the virtual environment and the at least one navigation instruction.

28. The robotic system according to claim 27, wherein a viewing angle of the rendering is aligned with an orientation of an instrument electrically connected to the robotic system.

29. The robotic system according to claim 18, wherein:
presenting, at the user interface electrically connected to the robotic system, comprises generating and displaying, by a graphical user interface (GUI) application, a plurality of two-dimensional icons according to the at least one set of navigation data and the virtual environment, and
the two-dimensional icons represent a position of an instrument electrically connected to the robotic system, the at least one navigation instruction, and a range of valid orientation of the instrument.

30. The robotic system according to claim 18, wherein:
the at least one navigation instruction is presented by a light indicator or an audio device, and
the light indicator and the audio device are electrically connected to the robotic system.

31. The robotic system according to claim 18, wherein the at least one navigation instruction is presented by a direction of the tool.

32. The robotic system according to claim 18, wherein:
presenting, at the user interface electrically connected to the robotic system, comprises generating and displaying, by a graphical user interface (GUI) application, a plurality of two-dimensional icons according to the at least one set of navigation data and the virtual environment, and
the two-dimensional icons represent a workspace progress bar.

33. The robotic system according to claim 18, wherein the instrument system is electrically connected to the computer system.

34. A navigation method for a medical operation and implemented by a robotic system using a tool, the method comprising:
receiving, at a processor of the robotic system, at least one set of navigation data, wherein:
the at least one set of navigation data includes at least one set of registration data, at least one set of instrument data, at least one set of spatial sensor data, and at least one set of medical operation plan data,
the at least one set of spatial sensor data includes information generated from signals transmitted from a spatial marker frame,
the robotic system includes an instrument of an instrument system, the instrument having a housing providing a manipulator, the manipulator having a platform coupled to the tool, a base, joints coupling the base and the platform, and actuators aligned parallel to each other, located inside the housing, and configured to drive movement of the joints, and the spatial marker frame disposed on the platform,
the at least one set of instrument data comprises at least one set of a virtual workspace of the robotic system or a virtual active space of the robotic system,
the at least one set of the virtual workspace or the virtual active space includes an object property corresponding to a workspace of the instrument,
the at least one set of the virtual workspace or the virtual active space includes a workspace of the manipulator,
the workspace of the manipulator includes a set of reachable points of the tool when the platform is driven by the joints while the base is remained static, and
the at least one set of navigation data comprises at least one virtual object used to generate a representation of an anatomical site and a representation of the instrument system;
receiving or generating, at the processor of the robotic system, at least one three-dimensional model of the at least one virtual object;
processing, at the processor of the robotic system, the at least one set of navigation data to generate a virtual environment, the virtual environment including the at least one set of the virtual workspace or the virtual active space and the at least one virtual object;
processing, at the processor of the robotic system, the at least one set of navigation data and the virtual environment to generate at least one navigation instruction, wherein:
at least one spatial relationship between at least two virtual objects in the virtual environment is determined,
a first virtual object of the at least two virtual objects is a virtual workspace or a virtual active space from the at least one set of instrument data and a second virtual object of the at least two virtual objects is a virtual planning object from the at least one set of medical operation plan data, the virtual planning object is a representation of a predetermined site of interaction between the tool and the anatomical site, and the at least one spatial relationship comprises at least one compensation rating, and the at least one compensation rating is calculated from the at least one set of medical operation plan data and the virtual workspace or from the at least one set of medical operation plan data and the virtual active space; and presenting, at a user interface electrically connected to the robotic system, at least one of the virtual environment and the at least one navigation instruction of the robotic system for reference during the medical operation, the robotic system obtaining the at least one compensation rating of the instrument.

\* \* \* \* \*